(12) United States Patent
Vriezen

(10) Patent No.: US 9,901,047 B2
(45) Date of Patent: Feb. 27, 2018

(54) SOLANUM LYCOPERSICUM PLANTS HAVING PINK FRUITS

(71) Applicant: NUNHEMS B.V., AB Nunhem (NL)

(72) Inventor: Willem Hendrik Vriezen, BM Haelen (NL)

(73) Assignee: NUNHEMS B.V., Nunhem (NL)

( * ) Notice: Subject to any disclaimer, the term of this patent is extended or adjusted under 35 U.S.C. 154(b) by 82 days.

(21) Appl. No.: 14/765,182

(22) PCT Filed: Jan. 28, 2014

(86) PCT No.: PCT/EP2014/051582
§ 371 (c)(1),
(2) Date: Jul. 31, 2015

(87) PCT Pub. No.: WO2014/118150
PCT Pub. Date: Aug. 7, 2014

(65) Prior Publication Data
US 2015/0366152 A1 Dec. 24, 2015

(30) Foreign Application Priority Data

Jan. 31, 2013 (EP) ...................................... 13153461

(51) Int. Cl.
| | |
|---|---|
| A01H 5/00 | (2006.01) |
| A01H 1/00 | (2006.01) |
| A01H 1/06 | (2006.01) |
| A01H 5/08 | (2006.01) |
| A01H 1/04 | (2006.01) |
| A23L 19/00 | (2016.01) |
| C12N 15/00 | (2006.01) |

(52) U.S. Cl.
CPC ................. *A01H 5/08* (2013.01); *A01H 1/04* (2013.01); *A23L 19/00* (2016.08); *A23V 2002/00* (2013.01)

(58) Field of Classification Search
None
See application file for complete search history.

(56) References Cited

U.S. PATENT DOCUMENTS

2011/0126313 A1* 5/2011 Luo ...................... C07K 14/415
800/278
2011/0289625 A1* 11/2011 Chen .................. C12N 15/8247
800/279

FOREIGN PATENT DOCUMENTS

WO 2009/157000 A1 12/2009

OTHER PUBLICATIONS

Adato et al., "Fruit-Surface Flavonoid Accumulation in Tomato Is Controlled by a S1MYB12-Regulated Transcriptional Network", PLOS Genetics, 2009, vol. 5, No. 12, e100777.
Luo et al., "AtMYB12 Regulates Caffeoyl Quinic Acid and Flavonol Synthesis in Tomato: Expression in Fruit Results in Very High Levels of Both Types of Polyphenol", The Plant Journal, 2008, vol. 56, No. 2, pp. 316-326
Mehrtens et al., "The *Arabidopsis* Transcription Factor MYB12 Is a Flavonol-Specific Regulator of Phenylpropanoid Biosynthesis", Plant Physiology, 2005, vol. 138, No. 2, pp. 1083-1096.
Lindstrom et al., "Inheritance in Tomatoes", Genetics 1925, vol. 10, pp. 305-317.
Lewinsohn et al., "Not Just Colors—Carotenoid Degradation as a Link Between Pigmentation and Aroma in Tomato and Watermelon Fruit", Trends in Food Science & Technology, 2005, vol. 16, pp. 407-415.
Ballester et al., "Biochemical and Molecular Analysis of Pink Tomatoes: Deregulated Expression of the Gene Encoding Transcription Factor S1MYB12 Leads to Pink Tomato Fruit Color", Plant Physiology, 2010, vol. 152, pp. 71-84.
Henikoff & Henikoff, "Amino acid substitution matrices from protein blocks", PNAS, 1992, vol. 89, pp. 10915-10919.
Solanum lycopersicum MYB12 (MYB12) mRNA, complete cds http://www.ncbi.nlm.nih.gov/nuccore/171466740, last visited on Jul. 29, 2015.
Sacks and Francis, "Genetic and Environmental Variation for Tomato Flesh Color in a Population of Modern Breeding Lines", J. Amer. Soc. Hort. Sci., 2001, vol. 126, No. 2, pp. 221-226.
Henikoff et al., "TILLING. Traditional Mutagenesis Meets Functional Genomics", Plant Physiology, 2004, vol. 135, pp. 630-636.
From TILLING http://tilling.ucdavis.edu/index.php/Tomato_Tilling, last visited on Jul. 29, 2015.
Till et al., "Discovery of chemically induced mutations in rice by TILLING", BMC Plant Biology, 2007, vol. 7, No. 19, pp. 1-12.
Till et al., "High-Throughput TILLING for *Arabidopsis*", Methods in Molecular Biology, 2006, vol. 323, pp. 127-135.
Till et al., "Discovery of induced point mutations in maize genes by TILLING", BMC Plant Biology, 2004, vol. 4, No. 12, pp. 1-8.
Till et al., "A protocol for TILLING and Ecotilling in plants and animals", Nature Protocols, 2006, vol. 1, No. 5, pp. 2465-2477.
Comai et al., "Efficient discovery of DNA polymorphisms in natural populations by Ecotilling", The Plant Journal, 2004, vol. 37, pp. 778-786.
Rigola et al., "High-Throughput Detection of Induced Mutations and Natural Variation Using KeyPointTM Technology", PLoS One, 2009, vol. 4, No. 3, e4761.
Mutschler et al., "Tomato Fruit Quality and Shelf Life in Hybrids Heterozygous for the alc Ripening Mutant", Hortscience, 1992, vol. 27, No. 4, pp. 352-355.
Mart1nez-Madrid et al. , "Polyamine Levels and Ethylene Production in Tomato Fruit Development and Ripening", Acta Horticulturae, 1995, vol. 412, pp. 463-469
Bui et al., "Postharvest Ripening Characterization of Greenhouse Tomatoes", International Journal of Food Properties, 2010, vol. 13, pp. 830-846.

(Continued)

*Primary Examiner* — Phoenix Bui
(74) *Attorney, Agent, or Firm* — Arent Fox LLP

(57) ABSTRACT

The present invention relates to cultivated plant of the species *Solanum lycopersicum* comprising a myb12 allele having one or more mutations, said mutations resulting in production of a mutant myb12 protein, fruits of such plants exhibiting a pink appearance.

25 Claims, 2 Drawing Sheets

(56) References Cited

OTHER PUBLICATIONS

U.S. Dept of Agrigulture, 1973, US standards for grades of fresh tomatoes, U.S. Dept Agr. Agr. Mktg. Serv., Washington D.C., pp. 1-10.

Liu et al., "There is more to tomato fruit colour than candidate carotenoid genes", Plant Biotechnology Journal, 2003, vol. 1, pp. 195-207.

Fish et al., "A Quantitative Assay for Lycopene That Utilizes Reduced Volumes of Organic Solvents", Journal of Food Composition and Analysis, 2002, vol. 15, pp. 309-317.

Clement et al., "Nondestructive Measurement of Fresh Tomato Lycopene Content and Other Physicochemical Characteristics Using Visible—NIR Spectroscopy", J. Agric. Food Chem., 2008, vol. 56, pp. 9813-9818.

Slimestad et al., "The Flavonoids of Tomatoes", J. Agric. Food Chem., 2008, vol. 56, pp. 2436-2441.

Bovy et al., "High-Flavonol Tomatoes Resulting from the Heterologous Expression of the Maize Transcription Factor Genes LC and C1", The Plant Cell, 2002, vol. 14, pp. 2509-2526.

Krieg, "Ethyl Methanesulfonate-induced reversion of bacteriophage T4rll Mutants", Genetics, 1963, vol. 48, pp. 561-580.

International Search Report and Written Opinion issued in International Patent Application No. PCT/EP2014/051582 dated Feb. 28, 2014 (12 pages).

* cited by examiner

| | | |
|---|---|---|
| WT Myb12 as in SEQ ID NO: 1) | MGRTPCCEKVGIKRGRWTAEEDQILTNYIISNGEGSWRSLPKNAGLLRCGKSCRLRWINYLRSDL<br>KRGNITSQEEDIIIKLHATLGNRWSLIAEHLSGRTDNEIKNYWNSHLSRKVDSLRIPSDEKLPKA<br>VVDLAKKGIPKPIKKSSISRPKNKKSNLLEKEALCCTNMPACDSAMELMQEDLAKIEVPNSWAGP<br>IEAKGSLSSDSDIEWPRLEEIMPDVVIDDEDKNTNFILNCFREEVTSNNVGNSYSCIEGNKKIS<br>SDDEKIKLLMDWQDNDELVWPTLPWELETDIVPSWPQWDDTDTNLLQNCTNDNNNYEEATTMEIN<br>NQNHSTIVSWLLS | 65<br>130<br>195<br>260<br>325<br>338 |
| Pink mutant 2961 (SEQ ID NO: 2) | MGRTPCCEKVGIKRGRWTAEEDQILTNYIISNGEGSWRSLPKNAGLLRCGKSCRLRWINY | 60 |
| Pink mutant 5505 (SEQ ID NO: 3) | MGRTPCCEKVGIKRGRWTAEEDQILTNYIISNGEGSWRSLPKNAGLLRCRKSCRLRWINYLRSDL<br>KRGNITSQEEDIIIKLHATLGNRWSLIAEHLSGRTDNEIKNYWNSHLSRKVDSLRIPSDEKLPKA<br>VVDLAKKGIPKPIKKSSISRPKNKKSNLLEKEALCCTNMPACDSAMELMQEDLAKIEVPNSWAGP<br>IEAKGSLSSDSDIEWPRLEEIMPDVVIDDEDKNTNFILNCFREEVTSNNVGNSYSCIEGNKKIS<br>SDDEKIKLLMDWQDNDELVWPTLPWELETDIVPSWPQWDDTDTNLLQNCTNDNNNYEEATTMEIN<br>NQNHSTIVSWLLS | 65<br>130<br>195<br>260<br>325<br>338 |
| 5058 (SEQ ID NO: 8) | MGRTPCCEKVGIKRGRWTAEEDQILTNYIISNGEGSWRSLPKNAGLLRCGKSCRLRWINYLRSDL<br>KRRNITSQEEDIIIKLHATLGNRWSLIAEHLSGRTDNEIKNYWNSHLSRKVDSLRIPSDEKLPKA<br>VVDLAKKGIPKPIKKSSISRPKNKKSNLLEKEALCCTNMPACDSAMELMQEDLAKIEVPNSWAGP<br>IEAKGSLSSDSDIEWPRLEEIMPDVVIDDEDKNTNFILNCFREEVTSNNVGNSYSCIEGNKKIS<br>SDDEKIKLLMDWQDNDELVWPTLPWELETDIVPSWPQWDDTDTNLLQNCTNDNNNYEEATTMEIN<br>NQNHSTIVSWLLS | 65<br>130<br>195<br>260<br>325<br>338 |
| 6899 (SEQ ID NO: 9) | MGRTPCCEKVGIKRGRWTAKEDQILTNYIISNGEGSWRSLPKNAGLLRCGKSCRLRWINYLRSDL<br>KRGNITSQEEDIIIKLHATLGNRWSLIAEHLSGRTDNEIKNYWNSHLSRKVDSLRIPSDEKLPKA<br>VVDLAKKGIPKPIKKSSISRPKNKKSNLLEKEALCCTNMPACDSAMELMQEDLAKIEVPNSWAGP<br>IEAKGSLSSDSDIEWPRLEEIMPDVVIDDEDKNTNFILNCFREEVTSNNVGNSYSCIEGNKKIS<br>SDDEKIKLLMDWQDNDELVWPTLPWELETDIVPSWPQWDDTDTNLLQNCTNDNNNYEEATTMEIN<br>NQNHSTIVSWLLS | 65<br>130<br>195<br>260<br>325<br>338 |

Figure 2

SEQUENCE LISTING

<160> NUMBER OF SEQ ID NOS: 9

<210> SEQ ID NO 1
<211> LENGTH: 338

<212> TYPE: PRT
<213> ORGANISM: Lycopersicon esculentum

<400> SEQUENCE: 1

```
Met Gly Arg Thr Pro Cys Cys Glu Lys Val Gly Ile Lys Arg Gly Arg
1               5                   10                  15

Trp Thr Ala Glu Glu Asp Gln Ile Leu Thr Asn Tyr Ile Ile Ser Asn
            20                  25                  30

Gly Glu Gly Ser Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Ser Gln Glu Glu Asp Ile Ile Ile Lys
65                  70                  75                  80

Leu His Ala Thr Leu Gly Asn Arg Trp Ser Leu Ile Ala Glu His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Val Asp Leu Ala Lys Lys Gly Ile Pro Lys Pro Ile Lys
    130                 135                 140

Lys Ser Ser Ile Ser Arg Pro Lys Asn Lys Ser Asn Leu Leu Glu
145                 150                 155                 160

Lys Glu Ala Leu Cys Cys Thr Asn Met Pro Ala Cys Asp Ser Ala Met
                165                 170                 175

Glu Leu Met Gln Glu Asp Leu Ala Lys Ile Glu Val Pro Asn Ser Trp
            180                 185                 190

Ala Gly Pro Ile Glu Ala Lys Gly Ser Leu Ser Ser Asp Ser Asp Ile
        195                 200                 205

Glu Trp Pro Arg Leu Glu Glu Ile Met Pro Asp Val Ile Asp Asp
    210                 215                 220

Glu Asp Lys Asn Thr Asn Phe Ile Leu Asn Cys Phe Arg Glu Glu Val
225                 230                 235                 240

Thr Ser Asn Asn Val Gly Asn Ser Tyr Ser Cys Ile Glu Glu Gly Asn
                245                 250                 255

Lys Lys Ile Ser Ser Asp Asp Gly Lys Ile Lys Leu Leu Met Asp Trp
            260                 265                 270

Gln Asp Asn Asp Glu Leu Val Trp Pro Thr Leu Pro Trp Glu Leu Glu
        275                 280                 285

Thr Asp Ile Val Pro Ser Trp Pro Gln Trp Asp Thr Asp Thr Asn
    290                 295                 300

Leu Leu Gln Asn Cys Thr Asn Asp Asn Asn Tyr Glu Glu Ala Thr
305                 310                 315                 320

Thr Met Glu Ile Asn Asn Gln Asn His Ser Thr Ile Val Ser Trp Leu
                325                 330                 335

Leu Ser
```

<210> SEQ ID NO 2
<211> LENGTH: 60
<212> TYPE: PRT
<213> ORGANISM: Lycopersicon esculentum

<400> SEQUENCE: 2

Met Gly Arg Thr Pro Cys Cys Glu Lys Val Gly Ile Lys Arg Gly Arg

```
            1               5                   10                  15
          Trp Thr Ala Glu Glu Asp Gln Ile Leu Thr Asn Tyr Ile Ile Ser Asn
                          20                  25                  30

Gly Glu Gly Ser Trp Arg Ser Leu Pro Lys Asn Ala Gly Leu Leu Arg
                      35                  40                  45

Cys Gly Lys Ser Cys Arg Leu Arg Trp Ile Asn Tyr
                  50                  55                  60

<210> SEQ ID NO 3
<211> LENGTH: 338
<212> TYPE: PRT
<213> ORGANISM: Lycopersicon esculentum

<400> SEQUENCE: 3

Met Gly Arg Thr Pro Cys Cys Glu Lys Val Gly Ile Lys Arg Gly Arg
          1               5                   10                  15

Trp Thr Ala Glu Glu Asp Gln Ile Leu Thr Asn Tyr Ile Ile Ser Asn
                          20                  25                  30

Gly Glu Gly Ser Trp Arg Ser Leu Pro Lys Asn Ala Gly Leu Leu Arg
                      35                  40                  45

Cys Arg Lys Ser Cys Arg Leu Arg Trp Ile Asn Tyr Leu Arg Ser Asp
                  50                  55                  60

Leu Lys Arg Gly Asn Ile Thr Ser Gln Glu Glu Asp Ile Ile Ile Lys
          65                  70                  75                  80

Leu His Ala Thr Leu Gly Asn Arg Trp Ser Leu Ile Ala Glu His Leu
                          85                  90                  95

Ser Gly Arg Thr Asp Asn Glu Ile Lys Asn Tyr Trp Asn Ser His Leu
                      100                 105                 110

Ser Arg Lys Val Asp Ser Leu Arg Ile Pro Ser Asp Glu Lys Leu Pro
                  115                 120                 125

Lys Ala Val Val Asp Leu Ala Lys Lys Gly Ile Pro Lys Pro Ile Lys
              130                 135                 140

Lys Ser Ser Ile Ser Arg Pro Lys Asn Lys Lys Ser Asn Leu Leu Glu
          145                 150                 155                 160

Lys Glu Ala Leu Cys Cys Thr Asn Met Pro Ala Cys Asp Ser Ala Met
                          165                 170                 175

Glu Leu Met Gln Glu Asp Leu Ala Lys Ile Glu Val Pro Asn Ser Trp
                      180                 185                 190

Ala Gly Pro Ile Glu Ala Lys Gly Ser Leu Ser Ser Asp Ser Asp Ile
                  195                 200                 205

Glu Trp Pro Arg Leu Glu Glu Ile Met Pro Asp Val Val Ile Asp Asp
              210                 215                 220

Glu Asp Lys Asn Thr Asn Phe Ile Leu Asn Cys Phe Arg Glu Glu Val
          225                 230                 235                 240

Thr Ser Asn Asn Val Gly Asn Ser Tyr Ser Cys Ile Glu Glu Gly Asn
                          245                 250                 255

Lys Lys Ile Ser Ser Asp Asp Glu Lys Ile Lys Leu Leu Met Asp Trp
                      260                 265                 270

Gln Asp Asn Asp Glu Leu Val Trp Pro Thr Leu Pro Trp Glu Leu Glu
                  275                 280                 285

Thr Asp Ile Val Pro Ser Trp Pro Gln Trp Asp Asp Thr Asp Thr Asn
              290                 295                 300

Leu Leu Gln Asn Cys Thr Asn Asp Asn Asn Tyr Glu Glu Ala Thr
          305                 310                 315                 320
```

Thr Met Glu Ile Asn Asn Gln Asn His Ser Thr Ile Val Ser Trp Leu
              325                 330                 335

Leu Ser

<210> SEQ ID NO 4
<211> LENGTH: 1017
<212> TYPE: DNA
<213> ORGANISM: Lycopersicon esculentum

<400> SEQUENCE: 4

| | | | | | | |
|---|---|---|---|---|---|---|
| atgggaagaa | caccttgttg | tgaaaaagtg | ggcatcaaga | gaggcagatg | gactgcagaa | 60 |
| gaagatcaaa | ttctcactaa | ttatattatt | tctaatggag | aaggctcttg | gaggtcgtta | 120 |
| cctaaaaatg | ccggattatt | gagatgcgga | aagagttgta | gactacgatg | gattaattat | 180 |
| ttgaggtctg | atctcaagag | agggaacatt | acttctcaag | aggaagatat | aattataaag | 240 |
| ttacatgcaa | ctttgggtaa | cagatggtct | cttatagcag | aacatttatc | aggtagaaca | 300 |
| gacaatgaga | taaaaaacta | ttggaactct | catctaagtc | gaaaagttga | tagcttaagg | 360 |
| ataccaagcg | atgagaagtt | acctaaagcc | gtagttgatt | tggctaaaaa | aggtataccg | 420 |
| aagccaatta | aaaatcatc | gattagtcga | ccaaaaaata | aaaagtcaaa | cttattagaa | 480 |
| aaagaagcat | tgtgttgtac | aaatatgcca | gcttgtgata | gtgccatgga | attaatgcaa | 540 |
| gaagatctag | caaagataga | ggtgccaaat | tcttgggcag | acctataga | ggccaaggga | 600 |
| agccttagtt | cagatagtga | tatcgaatgg | ccaagactcg | aggagattat | gccagacgtg | 660 |
| gtgattgatg | atgaagataa | gaacacaaat | ttcatattga | attgtttcag | agaagaagta | 720 |
| acgagcaata | atgtagggaa | tagttattca | tgtatcgagg | aaggtaataa | aaagatatca | 780 |
| agcgacgatg | aaaaaatcaa | attattaatg | gattggcaag | ataatgatga | gttagtatgg | 840 |
| ccaacgttac | catgggaatt | agaaacggat | atagttccca | gttggccaca | atgggacgat | 900 |
| actgacacta | acttacttca | aaattgcacc | aatgataata | ataattatga | agaagcaaca | 960 |
| acaatggaaa | ttaataacca | aaatcatagt | accattgtat | cttggctttt | gtcttag | 1017 |

<210> SEQ ID NO 5
<211> LENGTH: 1017
<212> TYPE: DNA
<213> ORGANISM: Lycopersicon esculentum

<400> SEQUENCE: 5

| | | | | | | |
|---|---|---|---|---|---|---|
| atgggaagaa | caccttgttg | tgaaaaagtg | ggcatcaaga | gaggcagatg | gactgcagaa | 60 |
| gaagatcaaa | ttctcactaa | ttatattatt | tctaatggag | aaggctcttg | gaggtcgtta | 120 |
| cctaaaaatg | ccggattatt | gagatgcgga | aagagttgta | gactacgatg | gattaattat | 180 |
| tagaggtctg | atctcaagag | agggaacatt | acttctcaag | aggaagatat | aattataaag | 240 |
| ttacatgcaa | ctttgggtaa | cagatggtct | cttatagcag | aacatttatc | aggtagaaca | 300 |
| gacaatgaga | taaaaaacta | ttggaactct | catctaagtc | gaaaagttga | tagcttaagg | 360 |
| ataccaagcg | atgagaagtt | acctaaagcc | gtagttgatt | tggctaaaaa | aggtataccg | 420 |
| aagccaatta | aaaatcatc | gattagtcga | ccaaaaaata | aaaagtcaaa | cttattagaa | 480 |
| aaagaagcat | tgtgttgtac | aaatatgcca | gcttgtgata | gtgccatgga | attaatgcaa | 540 |
| gaagatctag | caaagataga | ggtgccaaat | tcttgggcag | acctataga | ggccaaggga | 600 |
| agccttagtt | cagatagtga | tatcgaatgg | ccaagactcg | aggagattat | gccagacgtg | 660 |
| gtgattgatg | atgaagataa | gaacacaaat | ttcatattga | attgtttcag | agaagaagta | 720 |

| | |
|---|---|
| acgagcaata atgtagggaa tagttattca tgtatcgagg aaggtaataa aaagatatca | 780 |
| agcgacgatg aaaaaatcaa attattaatg gattggcaag ataatgatga gttagtatgg | 840 |
| ccaacgttac catgggaatt agaaacggat atagttccca gttggccaca atgggacgat | 900 |
| actgacacta acttacttca aaattgcacc aatgataata ataattatga agaagcaaca | 960 |
| acaatggaaa ttaataacca aaatcatagt accattgtat cttggctttt gtcttag | 1017 |

<210> SEQ ID NO 6
<211> LENGTH: 1017
<212> TYPE: DNA
<213> ORGANISM: Lycopersicon esculentum

<400> SEQUENCE: 6

| | |
|---|---|
| atgggaagaa caccttgttg tgaaaaagtg ggcatcaaga gaggcagatg gactgcagaa | 60 |
| gaagatcaaa ttctcactaa ttatattatt tctaatggag aaggctcttg gaggtcgtta | 120 |
| cctaaaaatg ccggattatt gagatgccga aagagttgta gactacgatg gattaattat | 180 |
| ttgaggtctg atctcaagag agggaacatt acttctcaag aggaagatat aattataaag | 240 |
| ttacatgcaa ctttgggtaa cagatggtct cttatagcag aacatttatc aggtagaaca | 300 |
| gacaatgaga taaaaaacta ttggaactct catctaagtc gaaaagttga tagcttaagg | 360 |
| ataccaagcg atgagaagtt acctaaagcc gtagttgatt tggctaaaaa aggtataccg | 420 |
| aagccaatta aaaaatcatc gattagtcga ccaaaaaata aaaagtcaaa cttattagaa | 480 |
| aaagaagcat tgtgttgtac aaatatgcca gcttgtgata gtgccatgga attaatgcaa | 540 |
| gaagatctag caaagataga ggtgccaaat tctgggcag gacctataga ggccaaggga | 600 |
| agccttagtt cagatagtga tatcgaatgg ccaagactcg aggagattat gccagacgtg | 660 |
| gtgattgatg atgaagataa gaacacaaat ttcatattga attgtttcag agaagaagta | 720 |
| acgagcaata atgtagggaa tagttattca tgtatcgagg aaggtaataa aaagatatca | 780 |
| agcgacgatg aaaaaatcaa attattaatg gattggcaag ataatgatga gttagtatgg | 840 |
| ccaacgttac catgggaatt agaaacggat atagttccca gttggccaca atgggacgat | 900 |
| actgacacta acttacttca aaattgcacc aatgataata ataattatga agaagcaaca | 960 |
| acaatggaaa ttaataacca aaatcatagt accattgtat cttggctttt gtcttag | 1017 |

<210> SEQ ID NO 7
<211> LENGTH: 5185
<212> TYPE: DNA
<213> ORGANISM: Lycopersicon esculentum
<220> FEATURE:
<221> NAME/KEY: exon
<222> LOCATION: (1034)..(1167)
<223> OTHER INFORMATION: Exon 1
<220> FEATURE:
<221> NAME/KEY: exon
<222> LOCATION: (1258)..(1386)
<223> OTHER INFORMATION: Exon 2
<220> FEATURE:
<221> NAME/KEY: exon
<222> LOCATION: (2824)..(3173)
<223> OTHER INFORMATION: Exon 3
<220> FEATURE:
<221> NAME/KEY: exon
<222> LOCATION: (3767)..(4170)
<223> OTHER INFORMATION: Exon 4

<400> SEQUENCE: 7

| | |
|---|---|
| gatgttgatc gaaagggagc gaatagagta cgttatttga ttttaaata ataatactcg | 60 |
| aggtttgaaa ataaaatttt agaacaatcg aaattgaggg tatcgaatat gtttaacctt | 120 |

```
aaaacggtac aattatttag atttatagac ttcaatcaag gacatatata aggattaaga      180
tagtcacaaa cacgtgattt gtatactata ttttgattaa tgaatgggca aattaaaatg      240
aaataacaaa tatatattta aacgagaca taaatacgtt aagtaaatag aattagttct      300
gaaatccgat gtcgatagct agcaacgtca tcgaataacc ttgattatat tggtattaat      360
tgaaacaaat ataacgtaga acaaattaag ctcaagatct taaaaacaca taagatatt      420 acattactac aaatgaatta aaaaatgcga taatttacaa tgaaggaaaa ggaatttttt      480
tattaagtaa aatcatagag taatcaccac ccactatgac tcccatctac ctggttaaag      540
aaaaattagc ataaaaaagt cttttatata tatatatata tatgaaagc aaagtgttct      600 aattatgaat aaagaaatat ttattagatt ataacgatga ttatatttag gatggagcta      660
gcaatttatc agaggattca cctcttttaa tgaaaaatat tattatctgt acataattaa      720
aatgattttt ttttataata tacaataaat atcaaattcc cttcaattat tttatacatt      780 tatttttta agttttaaat ttttttttat taaaaatctt aactcttctt ttatcaaaga      840
gtgacatgca atgcaaaaaa gcttattaag tcaacctttg gtacgttatt aagttcacat      900
aaaattaact agactaaagt gaagagcggg gtccatttat ttgtgttgtc tctctattta      960
ttggcatttc tattggtgaa atgagactaa ttttcattgc cttttgcttc tccattttgt     1020
gataataata ata atg gga aga aca cct tgt tgt gaa aaa gtg ggc atc        1069
            Met Gly Arg Thr Pro Cys Cys Glu Lys Val Gly Ile
            1               5                   10 aag aga ggc aga tgg act gca gaa gaa gat caa att ctc act aat tat       1117
Lys Arg Gly Arg Trp Thr Ala Glu Glu Asp Gln Ile Leu Thr Asn Tyr
        15                  20                  25 att att tct aat gga gaa ggc tct tgg agg tcg tta cct aaa aat gcc       1165
Ile Ile Ser Asn Gly Glu Gly Ser Trp Arg Ser Leu Pro Lys Asn Ala
    30                  35                  40 gg  tacgattacc tactaatctt ttattttaat ttgaaattta aaattttttt           1217
Gly
45 cttcgtttaa cagttttttt ataatatttt atttcgaagg a tta ttg aga tgc gga     1273
                                             Leu Leu Arg Cys Gly
                                                          50 aag agt tgt aga cta cga tgg att aat tat ttg agg tct gat ctc aag       1321
Lys Ser Cys Arg Leu Arg Trp Ile Asn Tyr Leu Arg Ser Asp Leu Lys
        55                  60                  65 aga ggg aac att act tct caa gag gaa gat ata att ata aag tta cat       1369
Arg Gly Asn Ile Thr Ser Gln Glu Glu Asp Ile Ile Ile Lys Leu His
        70                  75                  80 gca act ttg ggt aac ag  gtaattagtc aattacttga ttggactttt              1416
Ala Thr Leu Gly Asn Arg
            85 tagcttgcta attaaaccac tcattttgtt tcttttagt ctaggtccag aaaaaaatgt      1476 ctcctttaaa atcaagtact ttcttcgttt aaaaaataat aatttattt ttatttagtc      1536 tgttttataa agaatgactt tttttttagt aatatgttaa atttaatttt tcacatgaca     1596 tctttaaaat tataaaatta gagatagttt gatacatttg acataacttt aatttagaat     1656 cacttctttc ttttcttaaa atccgtttca agtcaaatag gtcattcttt tttatacgca     1716 agaagtattt ttttctttaa aaataaatct gaaactcatt ttaggttata aacattgtca     1776 caataatttg gtgcccgatc taacaacact tcttatatca tttagtgtg tgaatagtgt      1836 tacaccaaat ttaatacaac aaaattactc atcaaaatta ttactattca tgataacata     1896
```

```
gtgtaatgga ttcgagctag agaaagaata aataatatgt tttaggtaaa taatattaat    1956
ggattcgagc tagagaaaga ataaataata tgttttaggt aaataatatt ccatttgctt    2016
aaaaaaataa tcttttttt taaaaaaga atgatttctt ttactttcag atatatttta     2076
atctcagctg ttgttcgtgt gataagttta atatcatata atactttgct ttatttgaca    2136 taatttaat ttagatttat aaaattaata attttttta ttttcttaaa tatcgtgtta      2196
aattaaacta ggtcaatggt ataattgatt gaagtagatg ccctaataaa taaaagtgag    2256
atcaatgcaa ttataattaa cttaaattca tcacttcttt tttactactt gaattcatca    2316
cataaaacaa atgaattttt cttcttcttt tatttcatgt ttactccagt acttaatagt    2376
ttatagttat gtttgcctgg aaaaaggaga aaagttttgg tcactttaat ttgtagggta    2436
ttattttcta cattcattat ttgtgctaat gaattaataa gttaattaaa ttggtcccct    2496
cgagtaagtt caatattact ctttttttt tcttttcat atgacgagtg acatattcat      2556
gctttaaaaa caattcatcc tttctattat tagtcatata ccaagtctag aaaataaaac    2616
agtgacaatt taaagtattt tttcaaacta gaaaacgtat cttaagttgg atgtatacac    2676
aaatatatca ataatttca acaaagaaaa aatttagaaa agatgtgtta gttgtgagtt     2736
gtgacattaa atatgattga ttaatacaat ataccatcga tctagtttct aacattttct    2796
agtatcatcg acttttaaa attacag a tgg tct ctt ata gca gaa cat tta        2848
                              Trp Ser Leu Ile Ala Glu His Leu
                               90                   95 tca ggt aga aca gac aat gag ata aaa aac tat tgg aac tct cat cta      2896
Ser Gly Arg Thr Asp Asn Glu Ile Lys Asn Tyr Trp Asn Ser His Leu
        100                 105                 110 agt cga aaa gtt gat agc tta agg ata cca agc gat gag aag tta cct      2944
Ser Arg Lys Val Asp Ser Leu Arg Ile Pro Ser Asp Glu Lys Leu Pro
    115                 120                 125 aaa gcc gta gtt gat ttg gct aaa aaa ggt ata ccg aag cca att aaa      2992
Lys Ala Val Val Asp Leu Ala Lys Lys Gly Ile Pro Lys Pro Ile Lys
130                 135                 140 aaa tca tcg att agt cga cca aaa aat aaa aag tca aac tta tta gaa      3040
Lys Ser Ser Ile Ser Arg Pro Lys Asn Lys Lys Ser Asn Leu Leu Glu
145                 150                 155                 160 aaa gaa gca ttg tgt tgt aca aat atg cca gct tgt gat agt gcc atg      3088
Lys Glu Ala Leu Cys Cys Thr Asn Met Pro Ala Cys Asp Ser Ala Met
                165                 170                 175 gaa tta atg caa gaa gat cta gca aag ata gag gtg cca aat tct tgg      3136
Glu Leu Met Gln Glu Asp Leu Ala Lys Ile Glu Val Pro Asn Ser Trp
            180                 185                 190 gca gga cct ata gag gcc aag gga agc ctt agt tca g gtacaaattt          3183
Ala Gly Pro Ile Glu Ala Lys Gly Ser Leu Ser Ser
        195                 200 cgatgttttg actattttt attgtgaaat ttgattttaa aaaatatttt ttgatattaa     3243
agtgaaaaat aatattcaaa atttatttaa gttgtgtttg gttatgaata tgaattagag    3303
ttgttttttt cattttttcc tcaattattt cgagtaaacc ttttttttc tttaaagaat     3363 tgaaattta ttgtcaaata tgattctctg agttttaact atcgaaaaaa gcgaaaaga      3423 tcaaacaccc tctaatagtt tttattaatc aattaaatac attttcaata gtgactatga   3483
cgacataata tttatatatt gaaatatatg attatttat caaaaaactt aaaatttaat     3543
tttcacgtct ttcttttctt ttgaaacgtc attttttata tgtaccttt agatccaata     3603 tctatctatg gatagacgtt gcgaagtact ttttgttatt ttcaattatt aggcacaaat    3663
aattgaatct agcacctctt gtatgtacaa aattttaaac tgtagcaata aataaatata    3723
```

```
                                        cag  at   agt gat atc      3777
ttttttaatt ttttaaatt tttattttt tttgtctgag        Asp Ser Asp Ile
                                                         205 gaa tgg cca aga ctc gag gag att atg cca gac gtg gtg att gat gat    3825
Glu Trp Pro Arg Leu Glu Glu Ile Met Pro Asp Val Val Ile Asp Asp
    210                 215                 220 gaa gat aag aac aca aat ttc ata ttg aat tgt ttc aga gaa gaa gta    3873
Glu Asp Lys Asn Thr Asn Phe Ile Leu Asn Cys Phe Arg Glu Glu Val
225                 230                 235                 240 acg agc aat aat gta ggg aat agt tat tca tgt atc gag gaa ggt aat    3921
Thr Ser Asn Asn Val Gly Asn Ser Tyr Ser Cys Ile Glu Glu Gly Asn
                245                 250                 255 aaa aag ata tca agc gac gat gaa aaa atc aaa tta tta atg gat tgg    3969
Lys Lys Ile Ser Ser Asp Asp Glu Lys Ile Lys Leu Leu Met Asp Trp
            260                 265                 270 caa gat aat gat gag tta gta tgg cca acg tta cca tgg gaa tta gaa    4017
Gln Asp Asn Asp Glu Leu Val Trp Pro Thr Leu Pro Trp Glu Leu Glu
        275                 280                 285 acg gat ata gtt ccc agt tgg cca caa tgg gac gat act gac act aac    4065
Thr Asp Ile Val Pro Ser Trp Pro Gln Trp Asp Asp Thr Asp Thr Asn
    290                 295                 300 tta ctt caa aat tgc acc aat gat aat aat aat tat gaa gaa gca aca    4113
Leu Leu Gln Asn Cys Thr Asn Asp Asn Asn Asn Tyr Glu Glu Ala Thr
305                 310                 315                 320 aca atg gaa att aat aac caa aat cat agt acc att gta tct tgg ctt    4161
Thr Met Glu Ile Asn Asn Gln Asn His Ser Thr Ile Val Ser Trp Leu
                325                 330                 335 ttg tct tag aaatataata atatgacatt atatattgct tttgaatata            4210
Leu Ser ttactcaact cttttgttt cgttttatat ttggaatgtg ggaattagaa tgactagttt   4270
atgtacatat tttaagtttc gttagaaata tcgtcaagtc agattaaaat atgtatgagt  4330
tgatgtagta ataatgtta ttgttattac ttttttgat gtaattgaag tgtcttaatt    4390
tgattagaaa gtaaagttaa aatacagtga aatttttaa aaatttaatt ttttttgtt    4450 tagaatatca aattaatata atctaatta atttttaaaa ttaattaaat tgactttcga   4510
aaatggaaca tgaaattaa aagtggagaa gtagaaaaac actgacaaat taattaaaca   4570
aagaagaata aacaaatatg ctcataaact tggttttatt tagtatttat gatctttcaa  4630
ttacatataa gtagatattt aaatttgtat aaagttaaac aaataaatat catgtgacat  4690
attacacgta aaatatcatg taaacgtaaa ttgttatgca caacatgtat atttagttt   4750 ttaattcctt acaaaagaaa acatttaaag aaaaaaacta atcattaaaa atagacactt  4810
tattaaattg aacgaaataa aatactaaat tgagaaaaat aataattagg cttttataat  4870
acattgataa aacaaaccag atataacaca tgaatatgct cataaaagta gtctcattta  4930
atatatatat atatatatat atactaaaaa tttatataaa attatacaaa taaatatatg  4990
tcttacataa tatttcccga gaatcaataa gaaaataagt gctaagtttc agatcagtaa  5050
cgaactggct tcttgagaag ctcattccca ccgcacagct ccagcttgca accacagggg  5110
cccgtcaatt atcaaataaa aaagggcaac ttatttattc tacttattca atttttaata  5170
aatctaagta accat                                                   5185
```

<210> SEQ ID NO 8
<211> LENGTH: 338
<212> TYPE: PRT
<213> ORGANISM: Lycopersicon esculentum

<400> SEQUENCE: 8

```
Met Gly Arg Thr Pro Cys Cys Glu Lys Val Gly Ile Lys Arg Gly Arg
1               5                   10                  15

Trp Thr Ala Glu Glu Asp Gln Ile Leu Thr Asn Tyr Ile Ile Ser Asn
            20                  25                  30

Gly Glu Gly Ser Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ser Asp
    50                  55                  60

Leu Lys Arg Arg Asn Ile Thr Ser Gln Glu Asp Ile Ile Ile Lys
65                  70                  75                  80

Leu His Ala Thr Leu Gly Asn Arg Trp Ser Leu Ile Ala Glu His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Val Asp Leu Ala Lys Lys Gly Ile Pro Lys Pro Ile Lys
    130                 135                 140

Lys Ser Ser Ile Ser Arg Pro Lys Asn Lys Lys Ser Asn Leu Leu Glu
145                 150                 155                 160

Lys Glu Ala Leu Cys Cys Thr Asn Met Pro Ala Cys Asp Ser Ala Met
                165                 170                 175

Glu Leu Met Gln Glu Asp Leu Ala Lys Ile Glu Val Pro Asn Ser Trp
            180                 185                 190

Ala Gly Pro Ile Glu Ala Lys Gly Ser Leu Ser Ser Asp Ser Asp Ile
        195                 200                 205

Glu Trp Pro Arg Leu Glu Glu Ile Met Pro Asp Val Val Ile Asp Asp
    210                 215                 220

Glu Asp Lys Asn Thr Asn Phe Ile Leu Asn Cys Phe Arg Glu Glu Val
225                 230                 235                 240

Thr Ser Asn Asn Val Gly Asn Ser Tyr Ser Cys Ile Glu Glu Gly Asn
                245                 250                 255

Lys Lys Ile Ser Ser Asp Asp Glu Lys Ile Lys Leu Leu Met Asp Trp
            260                 265                 270

Gln Asp Asn Asp Glu Leu Val Trp Pro Thr Leu Pro Trp Glu Leu Glu
        275                 280                 285

Thr Asp Ile Val Pro Ser Trp Pro Gln Trp Asp Asp Thr Asp Thr Asn
    290                 295                 300

Leu Leu Gln Asn Cys Thr Asn Asp Asn Asn Tyr Glu Glu Ala Thr
305                 310                 315                 320

Thr Met Glu Ile Asn Asn Gln Asn His Ser Thr Ile Val Ser Trp Leu
                325                 330                 335

Leu Ser
```

<210> SEQ ID NO 9
<211> LENGTH: 338
<212> TYPE: PRT

<213> ORGANISM: Lycopersicon esculentum

<400> SEQUENCE: 9

```
Met Gly Arg Thr Pro Cys Cys Glu Lys Val Gly Ile Lys Arg Gly Arg
1               5                   10                  15
Trp Thr Ala Lys Glu Asp Gln Ile Leu Thr Asn Tyr Ile Ile Ser Asn
            20                  25                  30
Gly Glu Gly Ser Trp Arg Ser Leu Pro Lys Asn Ala Gly Leu Leu Arg
        35                  40                  45
Cys Gly Lys Ser Cys Arg Leu Arg Trp Ile Asn Tyr Leu Arg Ser Asp
    50                  55                  60
Leu Lys Arg Gly Asn Ile Thr Ser Gln Glu Asp Ile Ile Ile Lys
65                  70                  75                  80
Leu His Ala Thr Leu Gly Asn Arg Trp Ser Leu Ile Ala Glu His Leu
                85                  90                  95
Ser Gly Arg Thr Asp Asn Glu Ile Lys Asn Tyr Trp Asn Ser His Leu
            100                 105                 110
Ser Arg Lys Val Asp Ser Leu Arg Ile Pro Ser Asp Glu Lys Leu Pro
        115                 120                 125
Lys Ala Val Val Asp Leu Ala Lys Lys Gly Ile Pro Lys Pro Ile Lys
130                 135                 140
Lys Ser Ser Ile Ser Arg Pro Lys Asn Lys Lys Ser Asn Leu Leu Glu
145                 150                 155                 160
Lys Glu Ala Leu Cys Cys Thr Asn Met Pro Ala Cys Asp Ser Ala Met
                165                 170                 175
Glu Leu Met Gln Glu Asp Leu Ala Lys Ile Glu Val Pro Asn Ser Trp
            180                 185                 190
Ala Gly Pro Ile Glu Ala Lys Gly Ser Leu Ser Ser Asp Ser Asp Ile
        195                 200                 205
Glu Trp Pro Arg Leu Glu Glu Ile Met Pro Asp Val Val Ile Asp Asp
    210                 215                 220
Glu Asp Lys Asn Thr Asn Phe Ile Leu Asn Cys Phe Arg Glu Glu Val
225                 230                 235                 240
Thr Ser Asn Asn Val Gly Asn Ser Tyr Ser Cys Ile Glu Glu Gly Asn
                245                 250                 255
Lys Lys Ile Ser Ser Asp Asp Glu Lys Ile Lys Leu Leu Met Asp Trp
            260                 265                 270
Gln Asp Asn Asp Glu Leu Val Trp Pro Thr Leu Pro Trp Glu Leu Glu
        275                 280                 285
Thr Asp Ile Val Pro Ser Trp Pro Gln Trp Asp Asp Thr Asp Thr Asn
    290                 295                 300
Leu Leu Gln Asn Cys Thr Asn Asp Asn Asn Tyr Glu Glu Ala Thr
305                 310                 315                 320
Thr Met Glu Ile Asn Asn Gln Asn His Ser Thr Ile Val Ser Trp Leu
                325                 330                 335
Leu Ser
```

SOLANUM LYCOPERSICUM PLANTS HAVING PINK FRUITS

CROSS REFERENCE TO RELATED APPLICATIONS

This application is a 35 U.S.C. 371 National Phase of PCT Application No. PCT/EP2014/051582 filed Jan. 28, 2014, which claims benefit to European patent application No. 13153461.2 filed Jan. 31, 2013, the disclosure of which is hereby incorporated by reference in its entirety.

FIELD OF THE INVENTION

This invention relates to the field of plant biotechnology and plant breeding. Provided are cultivated *Solanum lycopersicum* plants comprising a myb12 allele having one or more mutations, said mutations resulting in production of a mutant myb12 protein, wherein said mutant myb12 protein has a G50R amino acid substitution in SEQ ID NO: 1, or in variants thereof having at least 85% amino acid sequence identity to SEQ ID NO: 1; or wherein said mutant myb12 protein comprises a deletion of the amino acids 61 to 338 in SEQ ID NO: 1, or in variants thereof, said variants having at least 85% amino acid sequence identity to SEQ ID NO: 1. The invention further provides tomato plants comprising an endogenous gene encoding a mutant myb12 protein of the invention, the fruits of which, exhibit a colorless epidermis and have a pink appearance at the late orange and red stages of fruit development. In addition the invention provides tomato fruit, seeds, pollen, plant parts, and progeny of the *Solanum lycopersicum* plants of the invention. The invention also provides tomato seeds from which the plants according to the invention can be grown and/or from which a mutant myb12 gene according to the invention can be obtained and introduced into any other tomato plant by traditional breeding, in order to generate other tomato plants producing pink fruits. Food and food products comprising or consisting of fruits of the plants of the invention are provided too. Also, methods of distinguishing plants, seeds, plant tissues and cells according to the invention and/or food and/or feed products made from these, from any other tomato plant, seed, tissue, cell, food or feed, are encompassed herein, whereby the presence of the mutant myb12 gene, mRNA (cDNA) and/or protein is detected.

The invention further provides an endogenous mutant myb12 gene, mRNA (cDNA) and/or myb12 protein encoded by said gene, having at least one human-induced non-transgenic mutation; and a method for producing plants of the invention.

BACKGROUND OF THE INVENTION

Skin color in tomato fruit is determined by the Y gene. Gene Y produces a distinct, yellow pigment suffused throughout the cell walls of the epidermis of the fruit, whereas its allelomorph, y, produces a transparent or colorless condition in the epidermal walls (E. W. Lindstrom, 1925, Inheritance in Tomatoes, Genetics, issue 10(4) pp 305-317).

Pink tomato fruit is very popular for consumption in Asia. The pink fruit was first described in fruit with a transparent epidermis lacking a yellow pigment (Lindstrom, 1925, Inheritance in Tomatoes, Genetics, issue 10 (4) pp 305-317). Genetic studies revealed that pink fruit result from the monogenic recessive y (yellow) locus present on chromosome 1, while red-colored fruit have the dominant Y allele (Lindstrom 1925). The Y gene has been identified as MYB12 (Ballester et al, vide infra).

The color of tomato fruit is mainly determined by carotenoids an flavonoids. The red color of ripe tomato fruit is due mainly to the accumulation of the carotenoid all-trans-lycopene, which is produced during fruit ripening. In addition to lycopene, tomato fruit contain significant levels of violaxanthin, and lutein. Tomato plants having mutation(s) in the carotenoid pathway have an altered carotenoid composition, which result in different fruit colors, such as orange (tangerine beta) or yellow (r) fruit (Lewinsohn et al. 2005 Trends Food Sci Technol., Vol 16 pp 407-415).

Additionally flavonoids play a role in determining the color of tomato fruit. Flavonoids accumulate predominantly in the fruit peel, since the flavonoid pathway is not active in the fruit flesh. One of the most abundant flavonoids in tomato fruit peel is the yellow-colored naringenin chalcone. In addition, up to 70 different flavonoids have been identified in tomato fruit.

Ballester et al. performed a phenotypic analysis of an introgression line (IL) population derived from a cross between *Solanum lycopersicum* "Moneyberg" and the wild species *Solanum chmielewskii* which revealed three ILs with pink fruit color. These ILs had a homozygous *S. chmielewskii* introgression on the short arm of chromosome 1, consistent with the position of the y (yellow) mutation known to result in colorless epidermis, and hence pink-colored fruit when combined with a red flesh. This same study revealed that the pink fruit lacked the ripening-dependent accumulation of the yellow-colored flavonoid naringenin chalcone in the fruit peel—which increased in the peel of Moneyberg fruit upon ripening-, while carotenoid levels were not affected (Ballester et al. 2010 Plant Physiology, vol 152 pp 71-84). In the same study Ballester et al. disclose (Ballester et al. 2010 Plant Physiology, vol 152 pp 77 right-hand column) that "the deduced amino acid sequence of the pink MYB12 alleles obtained from commercial sources was identical to the red Moneyberg allele", suggesting "that deregulated MYB12 gene expression", observed in all pink genotypes tested [by Ballester et al.], rather than aberrant MYB12 [protein] function is the primary cause of the pink phenotype. This cause of the pink color was confirmed using gene-silencing studies genetic mapping, segregation analysis, and VIGS (Virus Induced Gene Silencing) results.

Thus far, analysis of existing commercial non-GMO colorless peel (i.e. pink) y mutant revealed no mutations in the myb12 allele nor in its promotor sequence indicating that the y mutant phenotype is due to a mutation in a regulatory gene i.e. an additional mutant allele (Adato et al 2009 PLoS Genetics vol 5 issue 12 e1000777).

Despite the above, no alternative non-GMO pink mutants for tomato fruit have been found so far.

There is, thus, a need for alternative, non-GMO, cultivated tomato plants producing pink tomato fruit.

SUMMARY OF THE INVENTION

It was, surprisingly found by the inventors that cultivated plants of species *Solanum lycopersicum* having an aberrant MYB12 protein function, instead of a deregulated MYB12 gene expression, produced pink-appearing tomato fruits. This was very surprising, in view of Ballester et al. 2010 and Adato et al (2009) (supra).

The invention thus relates to a cultivated plant of the species *Solanum lycopersicum* comprising a myb12 allele having one or more mutations, said mutations resulting in production of a mutant myb12 protein, wherein said mutant myb12 protein has a G50R amino acid substitution in SEQ ID NO: 1, or in variants thereof, said variants having at least about 85% amino acid sequence identity to SEQ ID NO: 1; or wherein said mutant myb12 protein comprises a deletion of the amino acids 61 to 338 in SEQ ID NO: 1, or in variants thereof, said variants having at least about 85% amino acid sequence identity to SEQ ID NO: 1.

In one embodiment the invention relates to a cultivated tomato plant of the invention wherein said mutation or mutations in the genomic myb12 gene result in the fruits of said plant exhibiting a pink appearance at the late orange and red stages of fruit development.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of Myb12 protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA, hpRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

An "active protein" or "functional protein" is a protein which has protein activity as measurable in vitro, e.g. by an in vitro activity assay, and/or in vivo, e.g. by the phenotype conferred by the protein. A "wild type" Myb12 protein is a fully functional protein comprising at least about 85%, 90%, 95%, 96%, 97%, 98%, or 99% amino acid sequence identity to SEQ ID NO: 1 (also referred to as "variants" or "functional variants" of SEQ ID NO:1). Likewise, the wild type Myb12 allele is the allele encoding said wild type protein or wild type functional variant.

A "mutant myb12 protein" is herein a protein comprising one or more mutations in the nucleic acid sequence encoding the wild type Myb12 protein, whereby the mutation results in (the mutant nucleic acid molecule encoding) a "reduced-function" or "loss-of-function" protein, as e.g. measurable in vivo, e.g. by the modified phenotype conferred by the mutant allele. A "reduced function myb12 protein" or "reduced activity myb12 protein" or loss-of-function myb12 protein refers to a mutant myb12 protein which results in a colorless fruit epidermis, or colorless peel, which gives the ripe fruit a pink color when combined with the red tomato fruit flesh.

"Pink tomato fruit", "y mutant", "y phenotype", or "colorless peel y phenotype/mutant" or "colorless epidermis" or "colorless peel" refers to tomato fruit, or a tomato plant capable of producing fruit, having a less colored (less pigmented; more transparent) fruit epidermis e.g. when compared to the yellow/orange-colored normal epidermis (found in fruits of plants comprising one or two copies of the gene encoding the wild type Myb12 protein of SEQ ID NO:1 or functional variants), which result in pink appearance of the fruit when combined with red flesh. As the myb12 mutation is recessive, only the epidermis of fruits of tomato plants comprising the mutant myb12 allele in homozygous form will have the colorless peel. The color of the fruit epidermis can simply be compared visually, by looking at the fruits at the red stage and/or by peeling off the epidermis and visually assessing the pigmentation of the epidermis by e.g. holding the epidermis against a light source. Alternatively, the total flavonoid content or level of naringenin chalcone can be determined in the fruit peel tissue as described in Adato et al (supra) or Ballester et al. 2010 (supra). In particular, under Materials and Methods—Flavonoid and Carotenoid Extraction and HPLC Analysis, Ballester et al refer to Boni et al (2005) who describe a flavonoid and detection method in paragraph "Phenolic and ascorbic acid extraction", separation and detection by HPLC-PDA (page 429, left-hand column of Boni et al (2005) (Boni et al. New Phytologist (2005) volume 166 pp 427-438). The epidermis tissue (peel) of the colorless epidermis myb12 mutants comprises significantly less naringenin chalcone than peel of wild type fruits, e.g. less than 50 mg/kg fresh weight peel, preferably less than 20, 10, 5, 2, or less than 1 mg/kg fw of peel in the fruits homozygous for a mutant myb12 allele.

Epidermis refers to a single-layered group of cells that covers plants' leaves, flowers, fruits and stems. It forms a boundary between the plant and the external environment. The epidermis serves several functions, it protects against water loss, regulates gas exchange, secretes metabolic compounds, and (especially in roots) absorbs water and mineral nutrients Normal epidermis or epidermis of normal/red-colored tomato-fruit (i.e. of plants comprising the gene encoding the wild type Myb12 protein) has at the red-stage of ripening a yellow/orange color due to accumulation of yellow-colored flavonoid naringenin chalcone in the fruit epidermis, like for example in red varieties such as Moneyberg, Pusa Sheetal, Tapa, or TPAADASU, and many other tomato varieties grown in countries other than China.

A reduced function myb12 protein can be obtained by the transcription and translation of a "partial knockout mutant myb12 allele" which is, for example, a wild-type Myb12 allele, which comprises one or more mutations in its nucleic acid sequence. In one aspect, such a partial knockout mutant myb12 allele is a wild-type Myb12 allele, which comprises one or more mutations that preferably result in the production of a myb12 protein wherein at least one conserved and/or functional amino acid is substituted for another amino acid, such that the biological activity is significantly reduced but not completely abolished. However, other mutations, such as one or more non-sense, missense, splice-site or frameshift mutations in the tomato Myb12 allele may also result in reduced function myb12 protein and such reduced function proteins may have one or more amino acids replaced, inserted or deleted, relative to the wild type Myb12 protein. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis approaches, a target gene is the endogenous gene which is to be mutated, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which are joined to form a functional protein, which displays the functionality of the joined domains. A chimeric protein may also be a fusion protein of two or more proteins occurring in nature.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes both substance consumed to provide nutritional support for the human and animal body.

It is understood that comparisons between different plant lines involves growing a number of plants of a line (e.g. at least 5 plants, preferably at least 10 plants per line) under the same conditions as the plants of one or more control plant lines (preferably wild type plants) and the determination of statistically significant differences between the plant lines when grown under the same environmental conditions.

The "ripening stage" of a tomato fruit can be divided as follows: (1) Mature green stage: surface is completely green; the shade of green may vary from light to dark. (2) Breaker stage: there is a definite break in color from green to tannish-yellow, pink or red on not more than 10% of the surface; (3) Turning stage: 10% to 30% of the surface is not green; in the aggregate, shows a definite change from green to tannish-yellow, pink, red, or a combination thereof. (4) Pink stage: 30% to 60% of the surface is not green; in the aggregate, shows pink or red color. (5) Light red stage: 60% to 90% of the surface is not green; in the aggregate, shows pinkish-red or red. (6) Red stage: More than 90% of the surface is not green; in the aggregate, shows red color. It is noted that both normal tomato fruits (i.e. red when ripe) and pink fruits of the invention, have similar ripening stages. The color in the Red stage (6) will however be different: pink in fruits of the invention and red in normal (Wild type) tomato fruits.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty =10 and gap extension penalty =0.5 (both for nucleotide and protein alignments). For nucleotides the default scoring matrix used is DNA-FULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (world wide web at ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty =10, gap extension penalty =0.5, using scoring matrix DNAFULL for nucleic acids an Blosum62 for proteins).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

As used herein, the term "plant" includes the whole plant or any parts or derivatives thereof, such as plant organs (e.g., harvested or non-harvested fruits, flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries, fruits (e.g., harvested tissues or organs, such as harvested tomatoes or parts thereof), flowers, leaves, seeds, tubers, clonally propagated plants, roots, stems, cotyledons, hypocotyls, root tips and the like. Also any developmental stage is included, such as seedlings, immature and mature, etc. As used herein, the term plant includes plant and plant parts comprising one or more of the mutant myb12 alleles and/or myb12 proteins of the invention.

In another embodiment, the term plant part refers to plant cells, or plant tissues or plant organs; that comprise one or more of the mutant myb12 alleles and/or myb12 mRNA (cDNA) and/or myb12 protein of the invention. In one aspect a plant part can grow into a plant and/or live on photosynthesis (i.e. synthesizing carbohydrate and protein from the inorganic substance, such as water, carbon dioxide and mineral salt). In another aspect, a plant part cannot grow into a plant and/or live on photosynthesis (i.e. synthesizing carbohydrate and protein from the inorganic substance, such as water, carbon dioxide and mineral salt).

A "plant line" or "breeding line" refers to a plant and its progeny. As used herein, the term "inbred line" refers to a plant line which has been repeatedly selfed.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed) is the generation obtained from crossing two inbred parent lines. An "M1 population" is a plurality of mutagenized seeds/plants of a certain plant line or cultivar. "M2, M3, M4, etc." refers to the consecutive generations obtained following selfing of a first mutagenized seed/plant (M1).

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found. The Myb12 locus is thus the location in the genome where the Myb12 gene is found.

"Wild type allele" (WT or Wt) refers herein to a version of a gene encoding a fully functional protein (wild type protein). Such a sequence encoding a fully functional Myb12 protein is for example the wild type Myb12 cDNA (mRNA) sequence depicted in SEQ ID NO: 4, based on NCBI EU419748 *Solanum lycopersicum* MYB12 (MYB12) mRNA, complete cds world wide web at ncbi.nlm.nih.gov/nuccore/171466740 or the wild type Myb12 genomic sequence depicted in SEQ ID NO: 7. The protein sequence encoded by this wild type Myb12 mRNA is depicted in SEQ ID NO: 1. It consists of 338 amino acids. Other fully functional Myb12 protein encoding alleles (i.e. alleles which confer fruit coloring to the same extent i.e. red tomato fruit when the fruit is in ripe stage, as the protein of SEQ ID NO 1) may exist in other *Solanum lycopersicum* plants and may comprise substantial sequence identity with SEQ ID NO: 1, i.e. at least about 85%, 90%, 95%, 98%, 99%, 99.2%, 99.3%, 99.4%, 99.5%, 99.6%, 99.7% sequence identity with SEQ ID NO: 1. Such fully functional wild type Myb12 proteins are herein referred to as "variants" of SEQ ID NO: 1. Likewise the nucleotide sequences encoding such fully functional Myb12 proteins are referred to as variants of SEQ ID NO: 4 and SEQ ID NO: 7.

The following mutant myb12 alleles are exemplary of the myb12 mutants having a less colored epidermis of the tomato fruit at the late orange and/or red stages of fruit development and/or having pink tomato fruit, when in homozygous form, compared to *Solanum lycopersicum* being homozygous for the wild type Myb12 allele described in the present invention.

It is noted that nucleotide sequences referred to herein (SEQ ID NO: 4-6) are cDNA, i.e. coding DNA sequences, encoding the proteins of SEQ ID NO: 1-3. Counting A in the ATG of the START CODON as nucleotide position 1, SEQ ID's NO: 4-6 have 1017 nucleotides including the TAG STOP-codon. Obviously, when reference is made to these cDNA nucleotide sequences, it is understood that the cDNA is the coding region of the corresponding *Solanum lycopersicum* genomic myb12 sequence, which, however, additionally contains introns and therefore the nucleotides have different numbering. Thus, when reference is made to a tomato plant comprising an myb12 sequence according to e.g. any one of SEQ ID NO: 4-6, it is, therefore, understood that the tomato plant comprising the genomic myb12 sequence which comprises the coding DNA (cDNA), from which the mRNA of SEQ ID NO: 4-6 is transcribed (and which is in turn translated into protein). The mRNA has the same nucleotide sequence as the cDNA, except that Thymine (T) is Uracil (U) in the mRNA.

Further, when reference is made to a tomato plant comprising a nucleotide sequence encoding a protein according to the invention (i.e. a mutant protein of SEQ ID No: 2, or 3), this encompasses different nucleotide sequences, due to the degeneracy of the genetic code. In one embodiment the plant comprises the genomic Myb12 sequence depicted in SEQ ID NO:7 or a genomic Myb12 sequence substantially identical thereto (e.g. having at least about 70%, 75%, 80%, 85%, 90%, 95%, 98%, 99%, 99.2%, 99.3%, 99.4%, 99.5%, 99.6%, 99.7% sequence identity with SEQ ID NO: 7), but with one or more mutations in said sequence, especially in the exons of said genomic sequence (exon 1 ranges from nucleotide 1 to 134; exon 2 ranges from nucleotide 225 to 353, exon 3 ranges from nucleotide 1791 to 2140 and exon 4 ranges from nucleotide 2734 to 3137; counting A in the ATG of the START CODON as nucleotide position 1), encoding a mutant myb12 protein causing less-colored and/or colorless epidermis of the tomato fruit. In one embodiment said genomic sequence encodes the mutant protein of SEQ ID No: 2 or 3.

One exemplary mutant myb12 allele (mutant 2961) conferring, when in homozygous form, pink tomato fruit and/or less colored epidermis and/or colorless epidermis identified according to the present invention, comprises a mutation resulting in a truncated protein of 60 amino acid residues during translation, whereas the wild type protein has 338 amino acid residues (see SEQ ID NO: 1). The truncated protein sequence of mutant 2961 is depicted in SEQ ID NO: 2. The truncation is due to a change from thymine (T) to an adenine (A) at nucleotide 182 of SEQ ID NO: 4 counting A in the ATG of the START CODON as nucleotide position 1. This T182A mutation in mutant 2961 results in a change from a codon for leucine (i.e. Leu or L) (TTG) to a STOP-codon (TAG). The mutant cDNA is depicted in SEQ ID NO: 5.

Another exemplary mutant myb12 allele (mutant 5505) conferring, when in homozygous form, pink tomato fruit and/or less colored epidermis and/or colorless epidermis identified according to the present invention, comprises a mutation resulting in a change from glycine (Gly or G) to Arginine (Arg or R) at amino acid 50 in the encoded protein (SEQ ID NO: 3) i.e. a G50R mutation. The protein sequence of mutant 5505 is depicted in SEQ ID NO: 3. The amino acid substitution is due to a guanine (G) to cytosine (C) mutation at nucleotide 148 of SEQ ID NO: 4, counting A in the ATG of the START CODON as nucleotide position 1 (i.e. a G148C mutation). The mutant cDNA is depicted in SEQ ID NO: 6.

"Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified binding activity to nucleic acids or proteins, etc.

"Wild type plant" and "wild type fruits" or "normal ripening" plants/fruits refers herein to a tomato plant comprising two copies of a wild type (WT or Wt) Myb12 allele (Myb12/Myb12) encoding a fully functional Myb12 protein (e.g. in contrast to "mutant plants", comprising a mutant myb12 allele in homozygous form). Such plants are for example suitable controls in phenotypic assays. Preferably wild type and/or mutant plants are "cultivated tomato plants". For example the cultivar Moneymaker is a wild type plant, as is cultivar Ailsa Craig, cultivar Tapa and many others.

"Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

Wild relatives of tomato include *S. arcanum, S. chmielewskii, S. neorickii (=L. parviflorum), S. cheesmaniae, S. galapagense, S. pimpinellifolium, S. chilense, S. corneliomulleri, S. habrochaites (=L. hirsutum), S. huaylasense, S. sisymbriifolium, S. peruvianum, S. hirsutum* or *S. pennellii*.

"Average" refers herein to the arithmetic mean.

Colour and color are used interchangeably.

BRIEF DESCRIPTION OF THE SEQUENCE LISTING

SEQ ID NO: 1 shows the *Solanum lycopersicum* wild type, fully functional, MYB12 protein sequence as derived from the mRNA based on NCBI EU419748 *Solanum lycopersicum* MYB12 (MYB12) mRNA, complete cds world wide web at ncbi.nlm.nih.gov/nuccore/171466740.

SEQ ID NO: 2 shows the *Solanum lycopersicum* mutant 2961 myb12 protein sequence.

SEQ ID NO: 3 shows the *Solanum lycopersicum* mutant 5505 myb12 protein sequence.

SEQ ID NO: 4 shows the *Solanum lycopersicum* wild type Myb12 cDNA based on NCBI EU419748 *Solanum lycopersicum* MYB12 (MYB12) mRNA, complete cds world wide web at ncbi.nlm.nih.gov/nuccore/171466740.

SEQ ID NO: 5 shows the *Solanum lycopersicum* mutant 2961 myb12 cDNA sequence.

SEQ ID NO: 6 shows the *Solanum lycopersicum* mutant 5505 myb12 cDNA sequence.

SEQ ID NO: 7 shows the *Solanum lycopersicum* wild type Myb12 genomic DNA of the same source as under SEQ ID NO: 1 and 4.

SEQ ID NO: 8 shows the mutant 5058 Myb12 protein sequence, which does not affect fruit epidermis color.

SEQ ID NO: 9 shows mutant 6899 Myb12 protein sequence, which does not affect fruit epidermis color.

BRIEF DESCRIPTION OF THE FIGURES

FIG. 2: Table with amino acid sequences of Wt Myb12 protein (SEQ ID NO: 1), mutant 2961 myb12 protein (SEQ ID NO: 2), mutant 5505 myb12 protein (SEQ ID NO: 3) and the Myb12 protein of two other, non-pink, i.e. "normal red" plants, named 5058 (SEQ ID NO: 8) and 6899 (SEQ ID NO: 9).

DETAILED DESCRIPTION OF THE INVENTION

Figure 1:
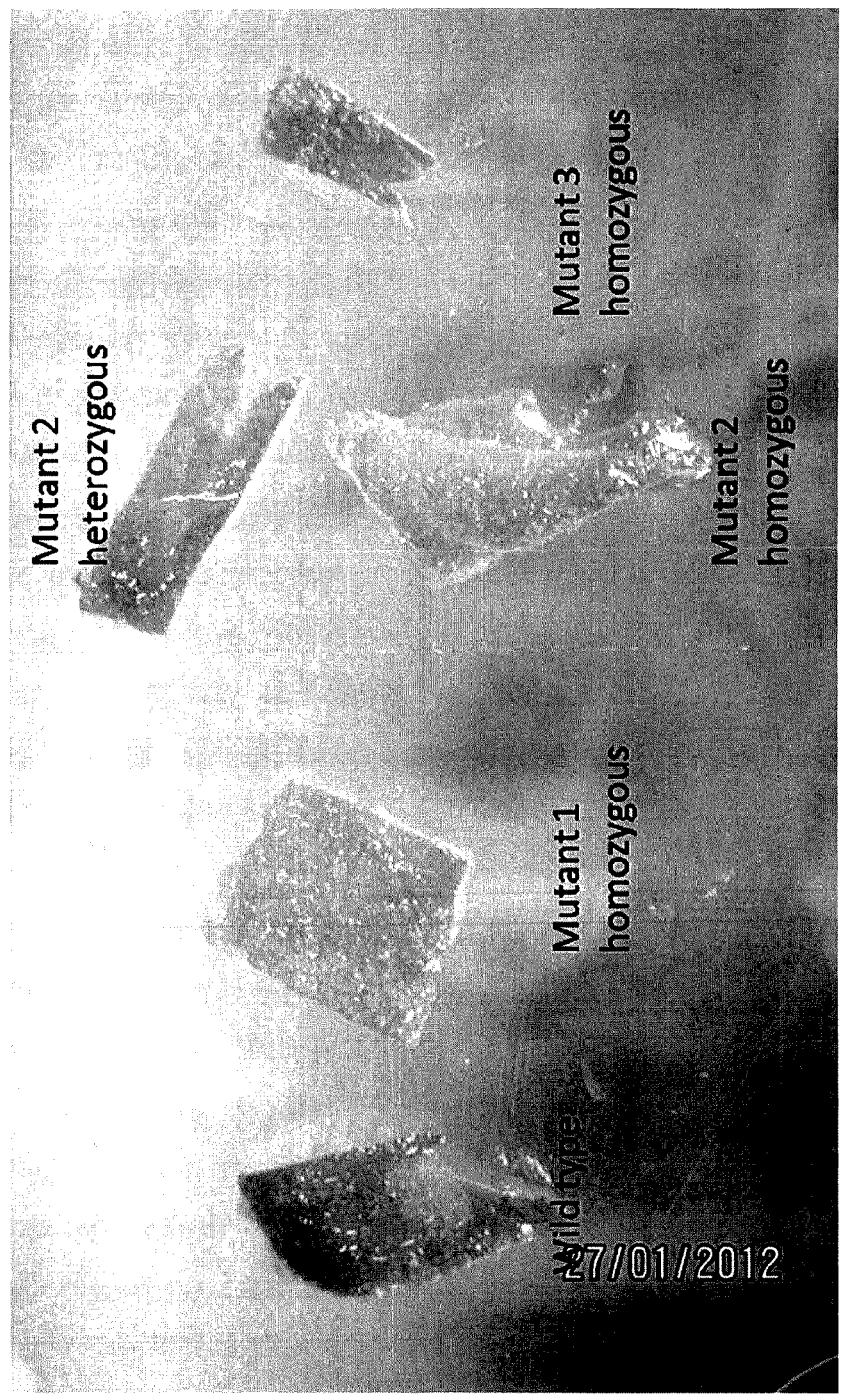
FIG. 1: Picture of tomato fruit peel (epidermis) of normal (wild type) and mutant fruit. Wild type fruits have a yellow/orange compound in the epidermis which is absent in mutant 1 (i.e. mutant 2961, homozygous for a myb12 allele encoding the protein of SEQ ID NO: 2), having a colorless peel. Mutant 2 (i.e. mutant 5505) shows a yellow/orange tomato fruit peel when the mutant myb12 allele is present in heterozygous form and a colorless peel when the mutant myb12 allele (encoding the protein of SEQ ID NO: 3) is in homozygous form. In homozygous form, the fruits are predominantly pink; only around the place where the fruit was connected to the plant, the epidermis does contain some yellow/orange compound while on the rest of the fruit, this compound is absent in the epidermis.

The invention discloses a cultivated plant of the species *Solanum lycopersicum* comprising a myb12 allele having one or more mutations (referred herein also to as "mutant myb12 allele"), said mutations resulting in production of a mutant myb12 protein, wherein said mutant myb12 protein has a G50R amino acid substitution in SEQ ID NO: 1 (i.e. relative to the wild type protein of SEQ ID NO:1), or in (functional) variants of SEQ ID NO:1 (i.e. relative to functional variants of the wild type protein of SEQ ID NO:1), said variants having at least about 85% amino acid sequence identity to SEQ ID NO: 1; or having at least about 90%, 93%, 95%, 96%, 97%, 98%, or 99% amino acid sequence identity to SEQ ID NO:1;
or wherein said mutant myb12 protein comprises a deletion of the amino acids 61 to 338 in SEQ ID NO: 1 (i.e. relative to the wild type protein of SEQ ID NO:1), or in (functional) variants thereof (i.e. relative to functional variants of the wild type protein of SEQ ID NO:1), said variants having at least about 85% amino acid sequence identity to SEQ ID NO: 1; or having at least about 90%, 93%, 95%, 96%, 97%, 98%, or 99% amino acid sequence identity to SEQ ID NO:1. In other words, the mutant myb12 protein comprises amino acids 1 to 60 of SEQ ID NO: 1, or amino acids 1 to 60 of a functional variant of SEQ ID NO: 1, said variant having at least about 85%, 90%, 93%, 95%, 96%, 97%, 98%, or 99% amino acid sequence identity to SEQ 1D NO: 1. When reference is made to mutant myb12 protein having a G50R amino acid substitution in (functional) variants of SEQ ID NO: 1, such (functional) variants of SEQ ID NO:1 have in addition to the G50R substitution at least about 85% amino acid sequence identity to SEQ ID NO: 1; or having at least about 90%, 93%, 95%, 96%, 97%, 98%, or 99% amino acid sequence identity to SEQ ID NO:1. In other words, the G50R substitution must be present in the variant of SEQ ID NO: 1, thereby rendering the variant to be a reduced function myb12 protein according to the invention.

Whether a variant of SEQ ID NO: 1 is functional can be tested phenotypically, i.e. by determining if the tomato plant which is homozygous for the allele encoding the variant of SEQ ID NO: 1 produces a colored (yellow-orange) epidermis on tomato fruits at the red-ripe stage of fruit development, in which case it is a functional Myb12 protein.

In one embodiment the invention relates to a cultivated tomato plant of the invention wherein said mutation or mutations result in the fruits of said plant exhibiting a pink appearance at the late orange and/or red stages of fruit development, when the mutant myb12 allele is in homozygous form.

In another embodiment, the invention relates to a cultivated tomato plant of the invention wherein said mutation or mutations result in the fruits of said plant exhibiting a pink appearance at the late orange and/or red stages of fruit development when compared to *Solanum lycopersicum* being homozygous for the wild type Myb12 allele, when the mutant myb12 allele is in homozygous form.

In yet another embodiment, the invention relates to a cultivated tomato plant of the invention wherein said mutation or mutations result in the fruits of said plant exhibiting a less colored epidermis than the epidermis of tomato plants homozygous for the wild type Myb12 allele (e.g. encoding the protein of SEQ ID NO: 1), or a colorless epidermis, of the tomato fruit at the late orange and/or red stages of fruit development, when the mutant myb12 allele is in homozygous form.

In an aspect, the invention relates to cultivated tomato plants comprising a myb12 allele as found in, and which is derivable from or obtainable from (or derived from or obtained from) seed deposited under accession number NCIMB 42087 or NCIMB 42088 in one or two copies, i.e. in homozygous or heterozygous form. In heterozygous form, the other allele may be a wild type Myb12 allele or another mutant myb12 allele, such as from any one of the other mutants provided herein, or any other mutant myb12 allele encoding for a loss-of-function myb12 protein or reduced-function myb12 protein as described herein. In heterozygous form, the other allele may, thus, be a reduced-function or a loss-of-function myb12 allele. If both alleles are reduced-function or loss-of-function myb12 alleles, the epidermis will be colorless, or have significantly reduced pigmentation, compared to plants homozygous for the wild type Myb12 allele or compared to plants comprising one copy (heterozygous) for a functional (wild type or variant) Myb12 allele.

In one aspect plants of the invention are obtainable by crossing a plant of which seeds where deposited under accession number NCIMB 42087 or NCIMB 42088 with another tomato plant.

In another aspect plants of the invention are obtainable from plants of which seeds where deposited under accession number NCIMB 42087 or NCIMB 42088 by crossing a plant grown from the seeds with another tomato plant.

In another aspect plants of the invention can be obtained by crossing a plant of which seeds where deposited under accession number NCIMB 42087 or NCIMB 42088 with another tomato plant.

The mutant myb12 allele of NCIMB 42087 or of NCIMB 42088, which confers a colorless peel phenotype when in homozygous form, can thus be transferred to any other tomato plant by traditional breeding, to generate pink fruited varieties, when transferring the allele to red-fleshed tomatoes. The mutant alleles can also be transferred to tomato plants producing other flesh-colors, such as yellow, green, orange, etc. There are several genetic loci which determine fruit flesh color (see Sacks and Francis 2001, J. Amer. Soc. Hort. Sci. 126(2): 221-226). However, in one aspect it is combined with tomato plants producing red fruit flesh color, to give the overall pink appearance of the fruit at red-ripe stage.

In yet another aspect plants of the invention comprise a mutant myb12 allele such as in seeds deposited under accession number NCIMB 42087 or NCIMB 42088.

In still another aspect plants of the invention are derivable by crossing a plant of which seeds where deposited under accession number NCIMB 42087 or NCIMB 42088 with another tomato plant.

In another aspect plants of the invention are derivable from plants of which seeds where deposited under accession number NCIMB 42087 or NCIMB 42088 with another tomato plant.

In another aspect plants of the invention can be derived by crossing a plant of which seeds where deposited under accession number NCIMB 42087 or NCIMB 42088 with another tomato plant.

In still another aspect, the plant of the invention is an F1 hybrid. The F1 hybrid preferably comprises two mutant myb12 alleles according to the invention. An F1 hybrid is made from two inbred parental lines, which are also an aspect of the invention, as these comprise at least one mutant myb12 allele, or optionally two mutant myb12 alleles (homozygous for myb12).

In another aspect, the myb12 allele having one or more mutations in the plant of the invention is present in homozygous form.

In one aspect the myb12 allele having one or more mutations in the plant of the invention is present in heterozygous form.

The invention also relates to seeds from which a plant according to the invention can be grown.

In another aspect the invention relates to a container comprising seeds from which a plant according to the invention can be grown.

In still another aspect the invention relates to plant parts of a plant of the invention comprising the myb12 allele comprising the one or more mutations.

In one aspect the invention relates to tomato fruit, seeds, pollen, plant parts, or progeny of the plant of the invention comprising the myb12 allele having one or more mutations said mutations resulting in production of a mutant myb12 protein, wherein said mutant myb12 protein has a G50R amino acid substitution in SEQ ID NO: 1 or in a variant thereof, said variant having at least about 85% amino acid sequence identity to SEQ ID NO: 1; or wherein said mutant myb12 protein comprises a deletion of the amino acids 61 to 338 in SEQ ID NO: 1, or in a variant thereof, said variant having at least 85% amino acid sequence identity to SEQ ID NO: 1.

The presence of one or two copies of a mutant myb12 allele according to the invention an any tomato plant tissue, cells, fruits, pollen, flowers, or other parts of a tomato plant can be determined using standard molecular biology techniques to detect the endogenous allele (genomic DNA), mRNA (cDNA) or protein present. For example, PCR, sequencing, ELISA assays or other techniques may be used.

The invention also relates to tomato fruit of a plant of the invention wherein the tomato fruit exhibit a pink appearance at the late orange and red stages of fruit development and the plant and plant parts are homozygous for a mutant myb12 allele according to the invention. In one aspect the invention relates to tomato fruit of a plant of the invention wherein the tomato fruit exhibit a pink appearance at the late orange and red stages of fruit development compared to Solanum lycopersicum being homozygous for the wild type Myb12 allele, e.g. an allele encoding the protein of SEQ ID NO:1.

In still another aspect the invention relates to food or food products comprising or consisting of fruits or parts of said fruit from plants of the invention. Again, the presence of one or two copies of the mutant myb12 alleles of the invention in the food or food products can be detected by standard molecular biology techniques, especially if the food or food product comprises or consists of fresh fruit tissue. In highly processed food products, such as tomato pastes, soups or sauces, it may be difficult to detect the mutant myb12 allele, or fragments thereof (genomic DNA fragments of the myb12 allele), or the mutant myb12 protein, as these may have been destroyed during the processing. In these products, analysis needs to be carried out at an earlier stage.

In another aspect the invention relates to compositions comprising fruit or parts of fruit from plants of the invention. Also a vegetative propagation of plants according to the invention are an aspect encompassed herein. Likewise harvested fruits and fruit parts, either for fresh consumption or for processing or in processed form are encompassed. Fruits may be graded, sized and/or packaged. Fruits may be sliced or diced or further processed The invention also relates to a method for producing a hybrid *Solanum lycopersicum* plant, said method comprising:
(a) obtaining a first *Solanum lycopersicum* plant of the invention (e.g. from any one of claims 1-7) or from seed from which a plant of the invention can be grown (e.g. according to claim 8); and
(b) crossing said first *Solanum lycopersicum* plant with a second *Solanum lycopersicum* plant to obtain hybrid seeds,
wherein said hybrid *Solanum lycopersicum* plant grown from said hybrid seeds comprises an myb12 allele having one or more mutations wherein said mutations result in production of a mutant myb12 protein, wherein said mutant myb12 protein has a G50R amino acid substitution in SEQ ID NO: 1 or in variants thereof having at least 85% amino acid sequence identity to SEQ ID NO: 1;
or wherein said mutant myb12 protein comprises a deletion of the amino acids 61 to 338 of SEQ ID NO: 1, or of variants thereof, said variants having at least 85% amino acid sequence identity to SEQ ID NO: 1.

In one aspect also the *Solanum lycopersicum* plant is a plant according to the invention, i.e. comprises at least one mutant myb12 allele according to the invention. The resulting F1 hybrid seeds, and plants grown from said seeds, comprise at least one, preferably two mutant myb12 alleles, preferably two identical myb12 alleles. The F1 hybrid seeds (and plants grown therefrom) are thus preferably homozygous for a myb12 allele of the invention.

In still another embodiment the mutant myb12 allele is derived from and/or generated in a cultivated tomato (e.g. a breeding line, variety or heirloom variety) or a wild relative of tomato. Such a human-induced mutation may, for example, be induced using targeted mutagenesis as described in EP1963505. Mutant myb12 alleles generated in wild relatives of tomato are then easily transferred into cultivated tomato by breeding.

In another aspect, the invention relates to a tomato plant of the invention having less colored epidermis and/or colorless epidermis and/or pink tomato fruit at the late orange or red stage of fruit development, when compared to wild type (Myb12/Myb12) plants, due to said plants comprising an endogenous myb12 allele, in homozygous form, encoding a loss-of-function myb12 protein or reduced-function myb12 protein, said myb12 protein having substantial sequence identity to SEQ. ID NO: 2 or to SEQ. ID NO: 3 or being 100% identical to the protein of SEQ ID NO: 2 or SEQ ID NO: 3.

In another embodiment the invention relates to an isolated protein having substantial sequence identity to SEQ. ID NO: 2 or to SEQ. ID NO: 3 or 100% sequence identity to SEQ.

ID NO: 2 or to SEQ. ID NO: 3. In still a further embodiment, the invention relates to an isolated nucleic acid sequence encoding a protein having substantial sequence identity to SEQ. ID NO: 2 or to SEQ. ID NO: 3 or 100% sequence identity to SEQ. ID NO: 2 or to SEQ. ID NO: 3.

In an even further embodiment, the invention relates to an isolated nucleic acid sequence, DNA or RNA, having substantial sequence identity to SEQ. ID NO: 5 or to SEQ. ID NO: 6 or having 100% sequence identity to SEQ. ID NO: 5 or to SEQ. ID NO: 6; or to an isolated nucleic acid sequence which is being transcribed into a nucleic acid sequence having substantial sequence identity to SEQ. ID NO: 5 or to SEQ. ID NO: 6 or having 100% sequence identity to SEQ. ID NO: 5 or to SEQ. ID NO: 6.

In still another aspect of the invention tomato plants are provided that have the same or similar epidermis and/or peel color at the red-ripe stage of fruit development as fruits of the tomato plants of the invention, of which representative seeds were deposited by Nunhems B.V. and accepted for deposit on 5 Dec. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42087 (mutant 2961) or NCIMB 42088 (mutant 5505).

According to a further aspect the invention provides a cell culture or a tissue culture of a tomato plant of the invention. The cell culture or tissue culture comprises regenerable cells. Such cells or tissues can be derived from leaves, pollen, embryos, cotyledon, hypocotyls, meristematic cells, roots, root tips, anthers, flowers, seeds or stems of tomato plants according to the invention. In another embodiment, the cell culture or tissue culture does not comprise regenerable cells.

An aspect of the invention is a method of producing a tomato plant of the invention comprising the steps of:
a. obtaining plant material, preferably seeds, of a tomato plant;
b. treating said plant material with a mutagen to create mutagenized plant material, e.g. mutagenized seeds;
c. analyzing said mutagenized plant material, e.g. the mutagenized seeds or progeny thereof obtained by selfing, to identify a plant having at least one mutation in at least one myb12 allele having substantial sequence identity to SEQ ID NO: 1 or in a functional variant thereof.

The method may further comprise analyzing the color of tomato fruits of the selected plant or progeny of the plant and selecting a plant of which the fruits have pink or pinkish color. In one aspect the mutation is selected from a mutation resulting in an amino acid substitution selected from the group consisting of G50R in SEQ ID NO: 1, or in variants thereof having at least 85% amino acid sequence identity to SEQ ID NO: 1; or wherein said mutant myb12 protein comprises a deletion of the amino acids 61 to 338 of SEQ ID NO: 1, or in variants thereof, said variants having at least 85% amino acid sequence identity to SEQ ID NO: 1.
In a further aspect, the mutation is selected from a mutation causing a change in the cDNA selected from the group consisting of G148C, and T182A in SEQ ID NO: 4.

In this method, the plant material of step a) is preferably selected from the group consisting of seeds, pollen, plant cells, or plant tissue of a tomato plant line or cultivar. Plant seeds being more preferred. In another aspect, the mutagen used in this method is ethyl methanesulfonate. In step b) and step c) the mutagenized plant material is preferably a mutant population, such as a tomato TILLING population.

Thus, in one aspect a method for producing a tomato plant comprising a mutant myb12 allele is provided comprising the steps of:
a) providing a tomato TILLING population,
b) screening said TILLING population for mutants in the myb12 gene, and
c) selecting from the mutant plants of b) those plants (or progeny of those plants) of which the fruits produce a colorless epidermis or reduced color epidermis compared to wild type (Myb12/Myb12) fruits.

Mutant plants (M1) are preferably selfed one or more times to generate for example M2 populations or preferably M3 or M4 populations for phenotyping in step c). In M2 populations the mutant allele is present in a ratio of 1 (homozygous for mutant allele): 2 (heterozygous for mutant allele): 1 (homozygous for wild type allele).

In yet a further aspect the invention relates to a method for producing a hybrid *Solanum lycopersicum* plant, said method comprising:
(a) obtaining a first *Solanum lycopersicum* plant of the current invention or from a seed from which a plant of the invention can be grown; and
(b) crossing said first *Solanum lycopersicum* plant with a second *Solanum lycopersicum* plant to obtain hybrid seeds,
wherein said hybrid *Solanum lycopersicum* plant comprises an myb12 allele having one or more mutations wherein said mutations result in production of a mutant myb12 protein which has a G50R amino acid substitution in SEQ ID NO: 1 or in variants thereof, said variants having at least 85% amino acid sequence identity to SEQ ID NO: 1;
or wherein said mutant myb12 protein comprises a deletion of the amino acids 61 to 338 of SEQ ID NO: 1, or of amino acids 61 to 338 (or amino acids 61 to the end of the protein) in variants of SEQ ID NO: 1, said variants having at least 85% amino acid sequence identity to SEQ ID NO: 1.

Plants and plant parts (e.g. fruits, cells, etc.) of the invention can be homozygous or heterozygous for the mutant myb12 allele.

Preferably, the plants according to the invention, which comprise one or more mutant myb12 alleles, and which produce a mutant myb12 protein having a G50R amino acid substitution in SEQ ID NO: 1 or in variants thereof having at least 85% amino acid sequence similarity to SEQ ID NO: 1;
or wherein said mutant myb12 protein comprises a deletion of the amino acids 61 to 338 in SEQ ID NO: 1, or in variants thereof, said variants having at least 85% amino acid sequence identity to SEQ ID NO: 1, do not produce fewer fruits than the wild type plants. Thus, fruit number per plant is preferably not reduced.

Other putative MYB12 genes/proteins can be identified in silico, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.).

In one embodiment loss-of-function myb12 protein or reduced-function mutant myb12 proteins (including variants or orthologs, such as myb12 proteins of wild tomato relatives) are provided and plants and plant parts comprising one or more myb12 alleles in their genome, which encode loss-of-function myb12 protein or reduced-function mutants, whereby the reduced-function confers pink tomato fruit (in combination of the homozygous myb12 mutant with red fruit flesh) and/or less colored epidermis and/or colorless epidermis, when the mutant allele is in homozygous form, compared to *Solanum lycopersicum* being homozygous for the wild type Myb12 allele.

In another embodiment mutant proteins are provided having at least about 85% amino acid sequence identity to SEQ ID NO: 1; or having at least about 90%, 93%, 95%, 96%, 97%, 98%, or 99%, or 100% amino acid sequence identity to SEQ ID NO:1. In another embodiment fragments of such mutant proteins are provided comprising 20, 25, 30, 35, 40, 45, 50, 55, 60, 70, 80, 90, 100, 120, or 150 contiguous amino acids of SEQ ID NO:1 or of the sequences having at least about 90%, 93%, 95%, 96%, 97%, 98%, or 99%, or 100% amino acid sequence identity to SEQ ID NO:1, including the G50R amino acid substitution in SEQ ID NO: 1. In still another embodiment, nucleic acid sequences encoding such proteins or protein fragments are provided.

In yet another embodiment, the use is provided of the mutant protein or variant thereof, or fragment thereof, as herein defined, in a tomato plant in order to obtain a colorless epidermis of the tomato fruit at the late orange and/or red stages of fruit development. This use is also provided of a nucleic acid encoding such a protein or protein fragment.

Any type of mutation may lead to a reduction in function of the encoded Myb12 protein, e.g. insertion, deletion and/or replacement of one or more nucleotides in the genomic DNA which comprises the cDNA (SEQ ID NO: 4, or variants thereof). However, not all mutations do cause a colorless epidermis as is illustrated in the Examples enclosed herein. In a preferred embodiment an myb12 nucleic acid sequence, encoding a loss-of-function myb12 protein or reduced-function myb12 protein due to one or more mutation(s), is provided, said myb12 protein causing pink tomato fruit (in combination of the homozygous myb12 mutant with red fruit flesh) and/or less colored epidermis and/or colorless epidermis e.g. when compared to *Solanum lycopersicum* being homozygous for the wild type Myb12 allele.

The in vivo loss-of-function myb12 protein or reduced-function of such proteins can be tested as described herein, by determining the effect this mutant allele, in homozygous form, has on the color of the epidermis of late orange or red-ripe stage tomato fruit or by determining the effect of the mutation on the color of the tomato fruits at late orange or red-ripe stage tomato fruit; when the homozygous mutant allele is combined with red fruit flesh the fruit color will become pink. Plants comprising a nucleic acid sequence encoding such mutant loss-of-function myb12 protein or reduced-function proteins and having less-colored epidermis and/or colorless epidermis and/or pink tomato fruit at late orange and/or red ripe stage optionally when compared to *Solanum lycopersicum* being homozygous for the wild type Myb12 allele can for example be generated de novo using e.g. mutagenesis and identified by TILLING or identified using EcoTILLING, as known in the art.

Also transgenic methods can be used to test in vivo functionality of a mutant myb12 allele encoding a mutant myb12 protein. A mutant allele can be operably linked to a plant promoter and the chimeric gene can be introduced into a tomato plant by transformation. Regenerated plants (or progeny, e.g. obtained by selfing), can be tested for epidermis color and/or tomato fruit color at late orange and/or red ripe stage. For example a tomato plant comprising a non-functional myb12 allele can be transformed to test the functionality of a transgenic myb12 allele.

TILLING (Targeting Induced Local Lesions IN Genomes) is a general reverse genetics technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as Myb12 according to the invention. Si nucleases, such as CEL1 or ENDO1, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, such as tomato. (see world wide web at tilling.ucdavis.edu/index,phpaomato_Tilling), rice (Till et al. 2007, BMC Plant Biol 7: 19), *Arabidopsis* (Till et al. 2006, Methods Mol Biol 323: 127-35),-*Brassica, maize* (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86).

In one embodiment of the invention (cDNA or genomic) nucleic acid sequences encoding such mutant myb12 proteins comprise one or more non-sense and/or missense mutations, e.g. transitions (replacement of purine with another purine (A ↔ G) or pyrimidine with another pyrimidine (C ↔ T)) or transversions (replacement of purine with pyrimidine, or vice versa (C/T ↔ A/G). In one embodiment the non-sense and/or missense mutation(s) is/are in the nucleotide sequence encoding any of the Myb12 exons, or an essentially similar domain of a variant Myb12 protein, i.e. in a domain comprising at least 80%, 90%, 95%, 98%, 99% amino acid sequence identity to amino acids of SEQ ID NO: 1 or to a variant thereof.

In one embodiment an myb12 nucleotide sequence comprising one or more non-sense and/or missense mutations in one of the exon-encoding sequence are provided, as well as a plant comprising such a mutant allele resulting in pink tomato fruit and/or less colored epidermis and/or colorless epidermis optionally when compared to *Solanum lycopersicum* being homozygous for the wild type Myb12 allele.

In a specific embodiment of the invention tomato plants and plant parts (fruits, seeds, etc.) comprising a mutant loss-of-function or reduced-function myb12 allele according to the invention are provided.

Also provided are nucleic acid sequences (genomic DNA, cDNA, RNA) encoding loss-of-function myb12 protein or reduced-function myb12 proteins, such as for example myb12 depicted in SEQ ID NO: 2, or 3 or variants thereof as defined above (including any chimeric or hybrid proteins or mutated proteins or truncated proteins). Due to the degeneracy of the genetic code various nucleic acid sequences may encode the same amino acid sequence. The nucleic acid sequences provided include naturally occurring, artificial or synthetic nucleic acid sequences. A nucleic acid sequence encoding Myb12 is provided for in SEQ ID NO: 4 (NCBI EU419748 Solanum lycopersicum MYB12 (MYB12) mRNA, complete cds world wide web at ncbi.nlm.nih.gov/nuccore/171466740).

It is understood that when sequences are depicted as DNA sequences while RNA is referred to, the actual base sequence of the RNA molecule is identical with the difference that thymine (T) is replace by uracil (U). When referring herein to nucleotide sequences (e.g DNA or RNA) italics are used, e.g. myb12 allele, while when referring to proteins, no italics are used, e.g. myb12 protein. Mutants are in small letters (e.g myb12 allele or myb12 protein), while wild type/functional forms start with a capital letter (Myb12 allele or Myb12 protein).

Also provided are nucleic acid sequences (genomic DNA, cDNA, RNA) encoding mutant myb12 proteins, i.e. loss-of-function myb12 protein or reduced function myb12 proteins, as described above, and plants and plant parts comprising such mutant sequences. For example, myb12 nucleic acid sequences comprising one or more non-sense and/or missense mutations in the wild type Myb12 coding sequence, rendering the encoded protein having a loss-of-function or reduced function in vivo. Also sequences with other mutations are provided, such as splice-site mutants, i.e. mutations in the genomic myb12 sequence leading to aberrant splicing of the pre-mRNA, and/or frame-shift mutations, and/or insertions (e.g. transposon insertions) and/or deletions of one or more nucleic acids.

It is clear that many methods can be used to identify, synthesise or isolate variants or fragments of myb12 nucleic acid sequences, such as nucleic acid hybridization, PCR technology, in silico analysis and nucleic acid synthesis, and the like. Variants of SEQ ID NO: 4, may either encode wild type, functional Myb12 proteins, or they may encode loss-of-function myb12 protein or reduced-function mutant alleles of any of these, as for example generated e.g. by mutagenesis and/or identified by methods such as TILLING or EcoTILLING, or other methods.

A plant of the invention can be used in a conventional plant breeding scheme to produce more plants with the same characteristics or to introduce the mutated myb12 allele into other plant lines or varieties of the same or related plant species.

Also transgenic plants can be made using the mutant myb12 nucleotide sequences of the invention using known plant transformation and regeneration techniques in the art. An "elite event" can be selected, which is a transformation event having the chimeric gene (comprising a promoter operably linked to a nucleotide sequence encoding a loss-of-function myb12 protein or reduced-function myb12 protein) inserted in a particular location in the genome, which results in good expression of the desired phenotype.

The plants of the invention as described above are homozygous for the mutant myb12 allele, or heterozygous. To generate plants comprising the mutant allele in homozygous form, selling can be used. The mutant myb12 alleles according to the invention can be transferred to any other tomato plant by traditional breeding techniques, such as crossing, selling, backcrossing, etc. Thus any type of tomato having comprising at least one mutant myb12 allele according to the invention can be generated. Any *S. lycopersicum* may be generated and/or identified having at least one mutant myb12 allele in its genome and producing a myb12 protein having loss-of-function myb12 protein or reduced activity compared to wild type Myb12 protein. The tomato plant may, thus, be any cultivated tomato, any commercial variety, any breeding line or other, it may be determinate or indeterminate, open pollinated or hybrid, producing fruit flesh of any color, fruits of any shape and size. The mutant allele generated and/or identified in a particular tomato plant, or in a sexually compatible relative of tomato, may be easily transferred into any other tomato plant by breeding (crossing with a plant comprising the mutant allele and then selecting progeny comprising the mutant allele).

The presence or absence of a mutant myb12 allele according to the invention in any tomato plant or plant part and/or the inheritance of the allele to progeny plants can be determined phenotypically and/or using molecular tools (e.g. detecting the presence or absence of the myb12 nucleotide sequence or myb12 protein using direct or indirect methods).

The mutant allele is in one embodiment generated or identified in a cultivated plant, but may also be generated and/or identified in a wild plant or non-cultivated plant and then transferred into an cultivated plant using e.g. crossing and selection (optionally using interspecific crosses with e.g. embryo rescue to transfer the mutant allele). Thus, a mutant myb12 allele may be generated (human induced mutation using mutagenesis techniques to mutagenize the target myb12 gene or variant thereof) and/or identified (spontaneous or natural allelic variation) in *Solanum lycopersicum* or in other *Solanum* species include for example wild relatives of tomato, such as *S. cheesmanii, S. chilense, S. habrochaites (L. hirsutum), S. chmielewskii, S. lycopersicum* x *S. peruvianum, S. glandulosum, S. hirsutum, S. minutum, S. parviflorum, S. pennellii, S. peruvianum, S. peruvianum* var. *humifusum* and *S. pimpinellifolium*, and then transferred into a cultivated *Solanum* plant, e.g. *Solanum lycopersicum* by traditional breeding techniques. The term "traditional breeding techniques" encompasses herein crossing, selling, selection, double haploid production, embryo rescue, protoplast fusion, transfer via bridge species, etc. as known to the breeder, i.e. methods other than genetic modification by which alleles can be transferred.

In another embodiment, the plant comprising the mutant myb12 allele (e.g. tomato) is crossed with another plant of the same species or of a closely related species, to generate a hybrid plant (hybrid seed) comprising the mutant myb12 allele. Such a hybrid plant is also an embodiment of the invention.

In one embodiment F1 hybrid tomato seeds (i.e. seeds from which F1 hybrid tomato plants can be grown) are provided, comprising at least one myb12 allele according to the invention, preferably two myb12 alleles. F1 hybrid seeds are seeds harvested from a cross between two inbred tomato parent plants. Such an F1 hybrid may comprise one or two mutant myb12 alleles according to the invention. Such an F1 hybrid comprising two mutant myb12 alleles according to the invention may comprise two copies of the same myb12 allele or two different myb12 alleles according to the invention. Thus, in one embodiment a plant according to the invention is used as a parent plant to produce an F1 hybrid.

Also a method for transferring a mutant myb12 allele to another plant is provided, comprising providing a tomato plant comprising a mutant myb12 allele in its genome, crossing said plant with another tomato plant and obtaining the seeds of said cross. Optionally plants obtained from these seeds may be further selfed and/or crossed and progeny selected comprising the mutant allele and/or, when the allele is in homozygous form producing fruits exhibiting a less colored or a colorless epidermis of the tomato fruit, or pink tomato fruit at the late orange and/or red stages of fruit development when the mutant allele is in homozygous form.

As mentioned, it is understood that other mutagenesis and/or selection methods may equally be used to generate mutant plants according to the invention. Seeds may for example be radiated or chemically treated to generate mutant populations. Also direct gene sequencing of myb12 may be used to screen mutagenized plant populations for mutant alleles. For example KeyPoint screening is a sequence based method which can be used to identify plants comprising mutant myb12 alleles (Rigola et al. PloS One, March 2009, Vol 4(3):e4761).

Thus, non-transgenic mutant tomato plants which produce lower levels of wild type Myb12 protein in fruits are provided, or which completely lack wild type Myb12 protein in fruits, and which produce loss-of-function myb12 protein or reduced-function myb12 protein in fruits due to one or more mutations in one or more endogenous myb12 alleles, are provided. These mutants may be generated by mutagenesis methods, such as TILLING or variants thereof, or they may be identified by EcoTILLING or by any other method. Myb12 alleles encoding loss-of-function Myb12 protein or reduced-functional Myb12 protein may be isolated and sequenced or may be transferred to other plants by traditional breeding methods.

Any part of the plant, or of the progeny thereof, is provided, including harvested fruit, harvested tissues or organs, seeds, pollen, flowers, ovaries, etc. comprising a mutant myb12 allele according to the invention in the genome. Also plant cell cultures or plant tissue cultures comprising in their genome a mutant myb12 allele are provided. Preferably, the plant cell cultures or plant tissue cultures can be regenerated into whole plants comprising a mutant myb12 allele in its genome. Also double haploid plants (and seeds from which double haploid plants can be grown), generated by chromosome doubling of haploid cells comprising an myb12 mutant allele, and hybrid plants (and seeds from which hybrid plants can be grown) comprising a mutant myb12 allele in their genome are encompassed herein, whereby in one aspect the double haploid plants and hybrid plants exhibit a less colored or colorless epidermis, of the tomato fruit at the late orange and/or red stages of fruit development when compared to *Solanum lycopersicum* being homozygous for the wild type Myb12 allele.

A plant part can be propagating or non-propagating, for example a non-propagating plant cell in particular a non-propagating plant cell comprising in its genome the mutant myb12 allele of the invention as discloses herein is provided.

The invention further relates to an endogenous myb12 protein having at least one human-induced non-transgenic mutation selected from G50R of SEQ ID NO: 1 or wherein said mutant myb12 protein comprises a deletion of the amino acids 61 to 338 of SEQ ID NO: 1, or in variants thereof, said variants having at least 85% amino acid sequence identity to SEQ ID NO: 1; or an endogenous myb12 allele encoding such protein.

Preferably, the mutant plants also have good other agronomic characteristics, i.e. they do not have reduced fruit numbers and/or reduced fruit quality compared to wild type plants. In a preferred embodiment the plant is a tomato plant and the fruit is a tomato fruit, such as a processing tomato, fresh market tomato of any shape or size or flesh color. Thus, also harvested products of plants or plant parts comprising one or two mutant myb12 alleles are provided. This includes downstream processed products, such as tomato paste, ketchup, tomato juice, cut tomato fruit, canned fruit, dried fruit, peeled fruit, etc. The products can be identified by comprising the mutant allele in their genomic DNA.

Seed Deposits

A representative sample of seeds of two (2) tomato TILLING mutants (myb12 mutants) according to Example 1, were deposited by Nunhems B.V. and accepted for deposit on 5 Dec. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42087 (mutant 2961) and NCIMB 42088 (mutant 5505).

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of tiling if the application is refused, abandoned, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

General Methods

PCR amplification products were directly sequenced by a service company (BaseClear, The Netherlands, world wide web at baseclear.com/) using the same primers as were used for the amplification. The obtained sequences were aligned using a computer program (CLC Bio Main Work Bench, Denmark, world wide web at cicbio.com) to identify the nucleotide changes.

Materials

Water used for analyses and mutagenis is tap water filtered in an Milli-Q water Integral system, Milli-Q type Reference A+ supplied with a Q-gard T2 Cartridge and a Quantum TEX Cartridge. Water resistance is >=18 MOhm.

Ethyl Methanesulfonate (EMS) (pure) was obtained from Sigma, product number M0880.

Measurement of Tomato Ripening and of Epidermis Color and/or Tomato Fruit Color

Tomato ripening can be measured by various methods known in the art like for example making periodically visual assessments of fruits and/or measurement of fruit firmness or softening, measurement of lycopene contents in the tomato fruits, ethylene production by the fruits, color of the fruits or any alternative method or combination of methods. Fruit firmness can for example be measured by evaluating resistance to deformation in units of for example 0.1 mm as measured with a penetrometer fitted with a suitable probe (e.g. a probe of 3 mm) (Mutschler et al, 1992, Hortscience 27 pp 352-355) (Martinez et al 1995 Acta Horticulturae 412 pp 463-469). Alternative methods exist in the art, such as use of a texturometer (Bui et al. 2010; International Journal of Food Properties, Volume 13, Issue 4 pp 830 846).

Fruit color can be classified by the U.S. standards for grades of fresh tomato (U.S. Dept of Agriculture, 1973, US standards for grades of fresh tomatoes, U.S. Dept Agr. Agr. Mktg. Serv., Washington D.C.), measuring the color with a chromometer (Mutschler et al, 1992, Hortscience 27 pp 352-355) or by comparing the color to a color chart like the Royal Horticultural Society (RHS) Color Chart (world wide web at rhs.org.uk).

Alternatively, external color of tomato fruit can be measured by a chromometer resulting in three parameters:

lightness, and chromaticity coordinates on a green to red scale and on a blue to yellow scale (Liu et al, 2003, Plant Biotechnology Journal 1, pp 195-207).

Lycopene content can be determined according to the reduced volumes method of Fish et al. A quantitative assay for lycopene that utilizes reduced volumes of organic solvents. Fish et al. *J. Food Compos. Anal.* 2002, 15, 309-317. This method can be used to determine lycopene content measured directly on intact tomato fruit while simultaneously estimating the basic physicochemical characteristics: color, firmness, soluble solids, acidity, and pH (Clement et al, *J. Agric. Food Chem.* 2008, 56, 9813-9818).

Flavonoid content can be determined according to the protocol provided in Ballester et al 2010 (vide supra) or Slimestad et al (Slimestad et al 2008, J. Agric. Food Chem. Vol 56, pp 2436-2441). Or, alternatively, flavonoids can be determined as aglycones or as their glycosides by preparing hydrolyzed and nonhydrolyzed extracts, respectively. Hydrolyzed extracts can be prepared and analyzed by HPLC with photodiode detection (25% acetonitrile in 0.1% trifluoroacetic acid). Dose-response curves of quercetin, naringenin, and kaempferol (0 to 20 g/mL) can be established to quantify these compounds in the hydrolyzed extracts. Nonhydrolyzed extracts can be prepared in 75% aqueous methanol with 10 min of sonication. Subsequent HPLC of the flavonoid species extracted can be done with a gradient of 5 to 50% acetonitrile in 0.1% trifluoroacetic acid. Absorbance spectra and retention times of eluting peaks can be compared with those of commercially available flavonoid standards as described in detail by Bovy et al (Bovy et al 2002, The Plant Cell vol 14 pp 2509-2526).

Fruit peel or epidermis was carefully separated from the rest of the tomato fruit (i.e. flesh of tomato fruit) using a scalpel. Color of fruit peel or epidermis was classified visually.

Example 1

Mutagenesis

A highly homozygous inbred line used in commercial processing tomato breeding was used for mutagenesis treatment with the following protocol. After seed imbibition on damp Whatman® paper for 24 h, 20,000 seeds, divided in 8 batches of 2500 respectively, were soaked in 100 ml of ultrapure water and ethyl methanesulfonate (EMS) at a concentration of 1% in conical flasks. The flasks were gently shaken for 16 h at room temperature. Finally, EMS was rinsed out under flowing water. Following EMS treatment, seeds were directly sown in the greenhouse. Out of the 60% of the seeds that germinated, 10600 plantlets were transplanted in the field. From these 10600 plantlets, 1790 were either sterile or died before producing fruit. For each remaining M1 mutant plant one fruits was harvested and its seeds isolated. The obtained population, named M2 population, is composed of 8810 seeds lots each representing one M2 family. Of these, 585 families were excluded from the population due to low seed set.

DNA was extracted from a pool of 10 seeds originating from each M2 seed lot. Per mutant line, 10 seeds were pooled in a Micronic® deepwell tube; world wide web at micronic.com-from a 96 deep-well plate, 2 stainless balls were added to each tube. The tubes and seeds were frozen in liquid nitrogen for 1 minute and seeds were immediately ground to a fine powder in a Deepwell shaker (Vaskon 96 grinder, Belgium; world wide web at vaskon.com) for 2 minutes at 16,8 Hz (80% of the maximum speed). 300 µl Agowa® Lysis buffer P from the AGOWA® Plant DNA Isolation Kit http.//www.agowa.de was added to the sample plate and the powder was suspended in solution by shaking 1 minute at 16,8 Hz in the Deepwell shaker. Plates were centrifuged for 10 minutes at 4000 rpm. 75 µl of the supernatant was pipetted out to a 96 Kingfisher plate using a Janus MDT® (Perkin Elmer, USA; world wide web at perkinelmer.com) platform (96 head). The following steps were performed using a Perkin Elmer Janus® liquid handler robot and a 96 Kingfisher® (Thermo labsystems, Finland; world wide web at thermo.com). The supernatant containing the DNA was diluted with binding buffer (150 µl) and magnetic beads (20 µl). Once DNA was bound to the beads, two successive washing steps were carried out (Wash buffer 1: Agowa wash buffer 1⅓, ethanol ⅓, isopropanol ⅓; Wash buffer 2: 70% ethanol, 30% Agowa wash buffer 2) and finally eluted in elution buffer (100 µl MQ, 0,025 µl Tween).

Grinding ten *S. lycopersicum* seeds produced enough DNA to saturate the magnetic beads, thus highly homogenous and comparable DNA concentrations of all samples were obtained. Comparing with lambda DNA references, a concentration of 30 ng/µl for each sample was estimated. Two times diluted DNA was 4 fold flat pooled. 2 µl pooled DNA was used in multiplex PCRs for mutation detection analysis.

Primers used to amplify gene fragments for HRM were designed using a computer program (Primer3, world wide web at primer3.sourceforge.net/). The length of the amplification product was limited between 200 and 400 base pairs. Quality of the primers was determined by a test PCR reaction that should yield a single product.

Polymerase Chain Reaction (PCR) to amplify gene fragments. 10 ng of genomic DNA was mixed with 4 µl reaction buffer (5× Reaction Buffer), 2 µl 10×LC dye ((LCGreen+ dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 10 µl. Reaction conditions were: 30 s 98° C., then 40 cycles of 10s. 98° C., 15 s 60° C., 25 s of 72° C. and finally 60 s at 72° C.

High Resolution Melt curve analysis (HRM) has been proven to be sensitive and high-throughput methods in human and plant genetics. HRM is a non-enzymatic screening technique. During the PCR amplification dye (LCGreen+ dye, Idaho Technology Inc., UT, USA) molecules intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that is recorded as a melting curve by the fluorescence detector. Pools containing a mutation form hetero duplexes in the post-PCR fragment mix. These are identified as differential melting temperature curves in comparison to homo duplexes.

The presence of the particular mutation in individual plants was confirmed repeating the HRM analysis on DNA from the individual M2 seed lots of the identified corresponding DNA pool. When the presence of the mutation, based on the HRM profile, was confirmed in one of the four individual M2 family DNA samples, the PCR fragments were sequenced to identify the mutation in the gene.

Once the mutation was known the effect of such an mutation was predicted using a computer program CODDLe (for Choosing codons to Optimize Discovery of Deleterious Lesions, world wide web at proweb.org/coddle/) that identifies the region(s) of a user-selected gene and of its coding sequence where the anticipated point mutations are most likely to result in deleterious effects on the gene's function.

Seeds from M2 families that contain mutations with predicted effect on protein activity were sown for phenotypic analysis of the plants.

Homozygous mutants were selected or obtained after selfing and subsequent selection. The effect of the mutation on the corresponding protein and phenotype of the plant was determined.

Seeds containing the different identified mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned leaving six flowers per inflorescence that were allowed to set fruit by self-pollination. The dates of fruit set of the first and sixth flower was recorded as was the date of breaker and red stage of the first and sixth fruit. At breaker of the sixth fruit the truss was harvested and stored in an open box in the greenhouse. Condition of the fruits was recorded during the whole ripening period.

At later stages fruit condition was determined based on visual assessment of the fruits and the date when the oldest fruit became 'bad' was recorded and further fruit deterioration was recorded (indicated by further fruit softness assessed by pinching the fruits, and visual assessment of dehydration/water loss, breaking of the skin and fungal growth).

The following mutants were identified: mutant 2961, mutant 5505, mutant 5058, mutant 6899, and seeds of the first two mutants were deposited at the NCIMB under the Accession numbers given above. The plants comprising variant Myb12 proteins 5058 and 6899 did not show a colorless peel phenotype and are therefore considered functional variants of Myb12.

The mutations in the nucleotide sequence compared to the cDNA of wild type Myb12 as depicted in SEQ ID NO 4, and its effect on the protein sequence of each mutant has been described above (mutant 2961 and 5505) and is also illustrated in FIG. 2. The protein sequence of mutants 5058 and 6899 is depicted in FIG. 2.

The observed T182A mutation in mutant 2961 and G148C mutation in mutant 5505 are remarkable in the sense that both mutation are less commonly seen in EMS mutants. EMS normally causes an ethylation of guanine leading to ethylguanine which causes pairing errors of ethylguanine with thymine. This results in G to A and C to T mutations (Krieg (1963) Genetics 48 pp 561-580).

Plants comprising mutations in the target sequence, such as the above mutant plants or plants derived therefrom (e.g. by selfing or crossing) and comprising the mutant myb12 allele, show a normal vegetative growth of all plant parts when compared to wild-type plants except for tomato fruit color of mutant 2961 and 5505. The other two mutants (5058 and 6899) have normal tomato fruit color when compared to wild type. The plants comprising mutations in the target sequence were screened phenotypically for their fruit color.

Example 2

Fruit Color Determination of Tomato Fruits

Seeds containing the different mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned, leaving six flowers per inflorescence that were allowed to set fruit by self-pollination. The dates of fruit set of the first and sixth flower was recorded as was the date of breaker and red stage of the first and sixth fruit. At red stage of the $4^{th}$ fruit the truss was harvested and stored in an open box in the greenhouse. Condition of the fruits was recorded during the whole ripening.

Color of the fruit and epidermis was determined visually at the late orange and red stage. Color of fruit and epidermis can for example be characterized by mapping the color to a color code of the color chart of the Royal Horticultural Society (RHS) world wide web at rhs.org.u1c/Plants/RHS-Publications/RHS-colour-charts.

Fruit of mutant 2961 (mutant 1 in FIG. 2, homozygous) had, at the red-ripe stage, a pink phenotype and a colorless and transparent epidermis. Fruit of mutant 5505 (mutant 2 in FIG. 2, homozygous) also had, at the red-ripe stage, a pink phenotype and a less colored/colorless and transparent epidermis. After some days in red stage, fruits of mutant 5505 (homozygous for the myb12 mutation) developed a small amount of the flavonoid present in the epidermis (i.e. skin) mainly on the shoulders of the fruit. Besides the pink fruit phenotype, both mutants did not have any other apparent pleiotropic effects to the plant.

Fruit of mutant 5505 (mutant 2 heterozygous in FIG. 2, heterozygous), heterozygous for the myb12 mutation (i.e. Myb12/myb12) had, at the red-ripe stage, a red fruit phenotype and an orange-colored epidermis.

Two other mutants were identified (5058 and 6899) in the population of Experiment 1 as described above. Tomato fruits of 5058 were red in the red stage of fruit development. Tomato fruits of mutant 6899 (mutant 3 in FIG. 2, homozygous) also had red fruits. The amino acid substitutions G68R and E20K do, therefore, not seem to affect protein function and these two mutants can be considered as being functional variants of Myb12.

All four (4) myb12 mutants identified comprise a mutation in the myb12 protein as shown in FIG. 2 and the mutated myb12 protein is produced in all of them. However, the effect of the mutation on the function of the myb12 protein differs: only two (2) of them have a pink phenotype which is caused by aberrant myb12 protein function. It thus appears that not all myb12 mutants result in a colorless peel and pink tomato fruit. The pink tomatoes of the invention comprise a particular genetical set-up which resulted in the colorless peel phenotype.

The invention claimed is:

1. A plant, fruit, seed, or part thereof of the species *Solanum lycopersicum* comprising a mutant myb12 allele that results in production of a mutant myb12 protein, wherein said mutant myb12 protein comprises a G50R amino acid substitution or comprises a deletion of the amino acids 61 to 338, the amino acid positions corresponding to SEQ ID NO: 1, wherein fruits of said plant comprise a less colored and/or colorless epidermis at the late orange and/or red stages of fruit development when said mutant myb12 allele is in homozygous form compared to fruit of a *Solanum lycopersicum* plant comprising a gene encoding a wild type myb12 protein, said wild type myb12 protein comprises at least 95% amino acid sequence identity to SEQ ID NO: 1.

2. The plant, fruit, seed, or part thereof according to claim 1, wherein said fruits of said plant exhibit a pink appearance at the late orange and/or red stages of fruit development when said mutant myb12 allele is in homozygous form.

3. The plant, fruit, seed, or part thereof according to claim 1, wherein the plant is obtained by crossing a plant of which seeds were deposited under Accession No. NCIMB 42087 with another tomato plant.

4. The plant, fruit, seed, or part thereof according to claim 1, wherein the plant is obtained by crossing a plant of which seeds were deposited under Accession No. NCIMB 42088 with another tomato plant.

5. The plant, fruit, seed, or part thereof according to claim 1, wherein the plant is an F1 hybrid plant.

6. The plant, fruit, seed, or part thereof according to claim 1, wherein said mutant myb12 allele is in homozygous form.

7. Seeds from which the plant according to claim 1 can be grown.

8. Tomato fruit or parts thereof, seeds, pollen, plant parts, or progeny of the plant of claim 1 comprising a mutant myb12 allele that results in production of a mutant myb12 protein, wherein said mutant myb12 protein comprises a G50R amino acid substitution or comprises a deletion of the amino acids 61 to 338, the amino acid positions corresponding to SEQ ID NO: 1,
wherein fruits of said plant comprise a less colored and/or colorless epidermis at the late orange and/or red stages of fruit development when said mutant myb12 allele is in homozygous form compared to fruit of a *Solanum lycopersicum* plant comprising a gene encoding a wild type myb12 protein, said wild type myb12 protein comprises at least 95% amino acid sequence identity to SEQ ID NO: 1.

9. The tomato fruit of claim 8, wherein the tomato fruit exhibits a pink appearance at the late orange and red stages of fruit development when said mutant myb12 allele is in homozygous form.

10. Food or food products comprising or consisting of fruits or parts thereof according to claim 8.

11. Compositions comprising fruit or parts thereof according to claim 8.

12. A method for producing a hybrid *Solanum lycopersicum* plant, said method comprising:
growing hybrid seeds obtained from crossing a first *Solanum lycopersicum* plant of claim 1 with a second *Solanum lycopersicum* plant to produce a hybrid *Solanum lycopersicum* plant,
wherein said hybrid *Solanum lycopersicum* plant comprises a mutant myb12 allele that results in production of a mutant myb12 protein, wherein said mutant myb12 protein comprises a G50R amino acid substitution or comprises a deletion of the amino acids 61 to 338, the amino acid positions corresponding to SEQ ID NO: 1,
wherein fruits of said hybrid *Solanum lycopersicum* plant comprise a less colored and/or colorless epidermis at the late orange and/or red stages of fruit development when said mutant myb12 allele is in homozygous form compared to fruit of a *Solanum lycopersicum* plant comprising a gene encoding a wild type myb12 protein, said wild type myb12 protein comprises at least 95% amino acid sequence identity to SEQ ID NO: 1.

13. The plant, fruit, seed, or part thereof according to claim 1, wherein fruits of said plant comprise a less colored and/or colorless epidermis at the red stage of fruit development when said mutant myb12 allele is in homozygous form compared to fruit of a *Solanum lycopersicum* plant comprising a gene encoding a wild type myb12 protein, said wild type myb12 protein comprises at least 95% amino acid sequence identity to SEQ ID NO: 1.

14. The plant, fruit, seed, or part thereof according to claim 1, wherein fruits of said plant exhibit a pink appearance at the red stage of fruit development when said mutant myb12 allele is in homozygous form.

15. The tomato fruit of claim 8, wherein the tomato fruit exhibits a pink appearance at the red stage of fruit development when said mutant myb12 allele is in homozygous form.

16. The tomato fruit of claim 8, wherein said mutant myb12 allele is in homozygous form.

17. The method according to claim 12, wherein fruits of said plant comprise a less colored and/or colorless epidermis at the red stage of fruit development when said mutant myb12 allele is in homozygous form compared to fruit of a *Solanum lycopersicum* plant comprising a gene encoding a wild type myb12 protein, said wild type myb12 protein comprises at least 95% amino acid sequence identity to SEQ ID NO: 1.

18. The method according to claim 12, wherein fruits of said plant exhibit a pink appearance at the red stage of fruit development when said mutant myb12 allele is in homozygous form.

19. The method of claim 12, wherein said mutant myb12 allele in said hybrid *Solanum lycopersicum* plant is in homozygous form.

20. The method of claim 12, wherein said mutant myb12 allele in said first *Solanum lycopersicum* plant is in homozygous form.

21. A method for producing hybrid *Solanum lycopersicum* seeds, comprising crossing a first *Solanum lycopersicum* plant of claim 1 with a second *Solanum lycopersicum* plant to obtain hybrid *Solanum lycopersicum* seeds comprising said mutant myb12 allele.

22. The method of claim 21, wherein said mutant myb12 allele in said first *Solanum lycopersicum* plant is in homozygous form.

23. A plant, fruit, seed, or part thereof of the species *Solanum lycopersicum* comprising a mutant myb12 allele that results in production of a mutant myb12 protein, wherein said mutant myb12 protein comprises a G50R amino acid substitution or comprises a deletion of the amino acids 61 to 338, the amino acid positions corresponding to SEQ ID NO: 1, and wherein said plant comprises a peel having less than 50 mg/kg fresh weight of naringenin chalcone.

24. The plant, fruit, seed, or part thereof of claim 1, wherein the deletion is due to a thymine to adenine mutation at position 182 of SEQ ID NO: 4, and the G50R substitution is due to guanine to cytosine mutation at position 148 of SEQ ID NO: 4.

25. A plant, fruit, seed, or part thereof of the species *Solanum lycopersicum* comprising a thymine to adenine mutation at position 182 of SEQ ID NO: 4, or guanine to cytosine mutation at position 148 of SEQ ID NO: 4.

* * * * *